US009200057B2

(12) United States Patent
Lauer et al.

(10) Patent No.: US 9,200,057 B2
(45) Date of Patent: Dec. 1, 2015

(54) METHODS AND COMPOSITIONS FOR INDUCING AN IMMUNE RESPONSE TO EGFRVIII

(75) Inventors: Peter M. Lauer, Albany, CA (US); Keith Bahjat, Portland, OR (US)

(73) Assignees: PROVIDENCE HEALTH & SERVICES-OREGON, Portland, OR (US); ADURO BIOTECH, Berkeley, CA (US)

( * ) Notice: Subject to any disclaimer, the term of this patent is extended or adjusted under 35 U.S.C. 154(b) by 0 days.

(21) Appl. No.: 13/988,076

(22) PCT Filed: Nov. 17, 2011

(86) PCT No.: PCT/US2011/061164
§ 371 (c)(1),
(2), (4) Date: Aug. 6, 2013

(87) PCT Pub. No.: WO2012/068360
PCT Pub. Date: May 24, 2012

(65) Prior Publication Data
US 2014/0037662 A1  Feb. 6, 2014

Related U.S. Application Data

(60) Provisional application No. 61/414,850, filed on Nov. 17, 2010.

(51) Int. Cl.
C12N 1/00       (2006.01)
C12N 7/00       (2006.01)
C07K 14/71      (2006.01)
A61K 39/00      (2006.01)
A61K 38/00      (2006.01)

(52) U.S. Cl.
CPC ............. *C07K 14/71* (2013.01); *A61K 39/0011* (2013.01); *A61K 38/00* (2013.01); *A61K 2039/522* (2013.01); *A61K 2039/523* (2013.01)

(58) Field of Classification Search
CPC .................................................... C07K 14/71
See application file for complete search history.

(56) References Cited

U.S. PATENT DOCUMENTS

| 5,709,999 | A | * | 1/1998 | Shattuck-Eidens et al. . 435/6.12 |
| 5,767,063 | A | | 6/1998 | Lee et al. |
| 5,830,702 | A | | 11/1998 | Portnoy et al. |
| 5,888,530 | A | | 3/1999 | Netti et al. |
| 6,051,237 | A | | 4/2000 | Paterson |
| 6,090,611 | A | | 7/2000 | Covacci et al. |
| 6,099,848 | A | | 8/2000 | Frankel et al. |
| 6,224,868 | B1 | | 5/2001 | Wong et al. |
| 6,379,943 | B1 | | 4/2002 | Graham et al. |
| 2004/0013690 | A1 | | 1/2004 | Portnoy et al. |
| 2004/0197343 | A1 | | 10/2004 | Dubensky, Jr. et al. |
| 2004/0228877 | A1 | | 11/2004 | Dubensky, Jr. et al. |
| 2005/0048081 | A1 | | 3/2005 | Frankel et al. |
| 2005/0249748 | A1 | | 11/2005 | Dubensky, Jr. et al. |

FOREIGN PATENT DOCUMENTS

| WO | 9614087 A1 | 5/1996 |
| WO | 9925376 A1 | 5/1999 |
| WO | 2004006837 A2 | 1/2004 |
| WO | 2007103225 A2 | 9/2007 |
| WO | 2007117371 A2 | 10/2007 |
| WO | 2009012488 A1 | 1/2009 |
| WO | 2009143085 A1 | 11/2009 |

OTHER PUBLICATIONS

Kesmir et al., Prediction of proteasome cleavage motifs by neural networks. J Protein Eng, 5, 31,55,65 Apr. 2002. vol. 15, No. 4, pp. 287-296.
Birkholz et al., Targeting of DEC-205 on human dendritic cells results in efficient MHC 11-restricted antigen presentation. Blood, Sep. 30, 2010, vol. 116, No. 13, pp. 2277-2285.
Net Chop. Net Chop 3.1 Server, Nov. 3, 2009 [online]. [Retrieved Mar. 7, 2012). 6 Retrieved from the Internet <URL: http://www.cbs.dtu.dk/services/NetChop/>.
International Search Report and Written Opinion issued on Mar. 29, 2013 in PCT/US2011/061164.
Paoletti, Applications of pox virus vectors to vaccination: An update. Proc Natl Acad Sci. USA Oct. 15, 1996;93 (21):11349-11353.
Parmiani et al., Cancer Immunotherapy With Peptide-Based Vaccines: What Have We Achieved? Where Are We Going? J Natl Cancer Inst. Jun. 5, 2002;94(11) 805-818.
Pellinen et al., Cancer cells as targets for lentivirus-mediated gene transfer and gene therapy. Int J Oncol. Dec. 2004;25(6):1753-1762.
Perri et al., An Alphavirus Replicon Particle Chimera Derived from Venezuelan Equine Encephalitis and Sindbis Viruses is a Potent Gene-Based Vaccine Delivery Vector. J Virol. Oct. 2003;77(19):10394-10403.
Polo and Dubensky, Virus-bases vectors for human vaccine applications. Drug Discov Today Jul. 1, 2002;7(13):719-727.
Polo et al., Stable alphavirus packaging cell lines for Sindbis virus- and Semliki Forest virus-derived vectors. Proc Natl Acad Sci. USA Apr. 13, 1999;96(8):4598-4603.
Quinnan et al., Protection of Rhesus Monkeys against Infection with Minimally Pathogenic Simian-Human Immunodeficiency Virus: Correlations with Neutralizing Antibodies and Cytotoxic T Cells. J Virol. Mar. 2005;76(6):3358-3369
Ramsay et al., DNA vaccination against virus infection and enhancement of antiviral immunity following consecutive immunization with DNA and viral vectors. Immunol Cell Biol. Aug. 1997;75(4):382-388.

(Continued)

*Primary Examiner* — Albert Navarro
(74) *Attorney, Agent, or Firm* — Michael A. Whittaker

(57) ABSTRACT

The present invention relates to methods of inducing a T-cell response against a EGFRvIII in a subject. These method comprise administering to a subject a composition which expresses at least one immunogenic polypeptide, the amino acid sequence of which comprise a plurality of EGFRvIII polypeptide sequences, the sequence of which each comprise EEKKGNYV (SEQ ID NO: 3), and/or administering the polypeptide itself.

21 Claims, 5 Drawing Sheets

(56) References Cited

OTHER PUBLICATIONS

Ripio et al., A Gly145Ser substitution in the transcriptional activator PrfA causes constitutive overexpression of virulence factors in Listeria monocytogenes. J Bacteriol. Mar. 1997;179(5):1533-1540
Roberts et al., Hexon-chimaeric adenovirus serotype 5 vectors circumvent pre-existing anti-vector immunity. Nature May 11, 2006;441(7090):239-243.
Rosenberg et al., Recombinant Fowlpox Viruses Encoding the Anchor-modified gp100 Melanoma Antigen Can Generate Antitumor Immune Responses in Patients with Metastatic Melanoma. Clin Cancer Res. Aug. 1, 2003;9(8):2973-2980.
Rozinov and Nolan, Evolution of peptides that modulate the spectral qualities of bound, small-molecule fluorophores. Chem Biol. Dec. 1998;5(12):713-728.
Santosuosso et al., Adenoviral Vectors for Mucosal Vaccination Against Infectious Diseases. Viral Immunol. 2005;18(2):283-291.
Schlesinger, Alphavirus vectors: development and potential therapeutic applications. Expert Opin Biol Ther. Mar. 2001;1(2)177-191.
Schwaab et al., Immunological Effects of Granulocyte-Macrophage Colony-Stimulating Factor and Autologous Tumor Vaccine in Patients with Renal Cell Carcinoma. J Urol. Mar. 2004;171(3):1036-1042.
Sepulveda-Amor et al., A randomized trial demonstrating successful boosting responses following simultaneous aerosols of measles and rubella (MR) vaccines in school age children Vaccine. Jun. 21, 2002;20(21-22):2790-2795.
Shafferman et al., Alphavirus hybrid virion vaccines. Adv Exp Med Biol. 1996;397:41-47.
Shen et al., Recombinant Listeria monocytogenes as a live vaccine vehicle for the induction of protective anti-viral cell-mediated immunity. Proc. Natl Acad Sci U S A. Apr. 25, 1995;92(9):3987-3991.
Shetron-Rama et al., Isolation of Listeria monocytogenes mutants with high-level in vitro expression of host cytosol-induced gene products. Mol Microbiol. Jun. 2003;48(6):1537-1551.
Sinnathamby et al., Priming and activation of human ovarian and breast cancer-specific CD8+ T cells by polyvalent Listeria monocytogenes-based vaccines. J Immunother. Oct. 2009:32(8):856-869
Skinner et al., Fowlpox virus as a recombinant vaccine vector for use in mammals and poultry. Expert Rev Vaccines Feb. 2005;4(1):63-76.
Skoble et al., Three Regions within Acta Promote Arp2/3 Complex-Mediated Actin Nucleation and Listeria monocytogenes Motility. J Cell Biol. Aug. 7, 2000;150(3):527-538.
Smith and Thorpe, Diversity in the serine recombinases. Mol Microbiol. Apr. 2002;44(2):299-307.
Smith et al., Measurement of Cell-Mediated Immunity With a Varicella-Zoster Virus-specific Interferon-g ELISPOT Assay: Responses in an Elderly Population Receiving a Booster Immunization. J Med Virol. 2003;70 Suppl 1:S38-S41.
Snyder et al., Protection against Lethal Vaccinia Virus Challenge in HLA-A2 Transgenic Mice by Immunization with a Single CD8+ T-Cell Peptide Epitope of Vaccinia and Vanola Viruses. J Virol. Jul. 2004;78(13):7052-7060.
Song et al., Characterization of Immune Responses Induced by Intramuscular Vaccination with DNA Vaccines Encoding Measles Virus Hemagglutinin and/or Fusion Proteins. J Virol. Aug. 2005;79(15):9854-9861.
Strugnell et al., DNA vaccines for bacterial infections. Immunol Cell Biol. Aug. 1997;75(4):364-369.
Sumida et al., Recruitment and expansion of dendritic cells vivo potentiate the immunogenicity of plasmid DNA vaccines. J Clin Invest. Nov. 2004;114(9):1334-1342.
Tai et al., Curative Potential of GM-CSF-Secreting Tumor Cell Vaccines on Established Orthotopic Liver Tumors: Mechanisms for the Superior Antitumor Activity of Live Tumor Cell Vaccines. J Biomed Sci. Mar.-Apr. 2004;11 (2):228-238.
Tatsis and Ertl, Adenoviruses as Vaccine Vectors. Mol Ther Oct. 2004;10(4):616-629.

Thiry et al., Recombination in the alphaherpesvirus bovine herpesvirus 1. Vet Microbiol. Mar. 31, 2006;113(3-4):171-177.
Toes et al., Discrete Cleavage Motifs of Constitutive and Immunoproteasornes Revealed by Quantitative Analysis of Cleavage Products. J Exp Med. Jul. 2, 2001;194(1):1-12.
Trapp et al., Potential of Equine Herpesvirus 1 as a Vector for Immunization. J Virol. May 2005;79(9):5445-5454.
Trimble et al., Comparison of the CD8+ T cell responses and antitumor effects generated by DNA vaccine administered through gene gun, biojector, and syringe. Vaccine Sep. 8, 2003;21(25-26):4036-4042.
Tuting, The immunology of cutaneous DNA immunization. Curr Opin Mol Ther. Apr. 1999;1(2):216-225
Vanniasinkam and Ertl, Adenoviral gene delivery for HIV-1 vaccination. Curr Gene Ther. Apr. 2005;5(2):203-212.
Vasir et al., Fusion of dendritic cells with multiple myeloma cells results in maturation and enhanced antigen presentation. Br J Haematol. Jun. 2005;129(5):687-700.
Vazquez-Boland et al., Nucleotide sequence of the lecithinase operon of Listeria monocytogenes and possible role of lecithinase in cell-to-cell spread. Infect Immun. Jan. 1992;60(1):219-230
Vieweg and Dannull., Tumor vaccines: from gene therapy to dendritic cells—the emerging frontier. Urol Clin North Am Aug. 2003;30(3):633-643.
Wesikirch and Paterson, Listeria monocytogenes: a potent vaccine vector for neoplastic and infectious disease. Immunol Rev. Aug. 1997;158:159-169.
Williamson et al., Characterization and Selection of H1V-1 Subtype C Isolates for Use in Vaccine Development. AIDS Res Hum Retroviruses. Feb. 2003;19(2):133-144.
Wong and Freitag, A Novel Mutation within the Central Listeria monocytogenes Regulator PrfA That Results in Constitutive Expression of Virulence Gene Products J Bacteriol. Sep. 2004;186(18):6265-6276.
Woycechowsky and Raines, Native Disulfide Bond Formation in Proteins. Curr Opin Chem Biol. Oct. 2000;4(5):533-539.
Wu et al., Construction and Characterization of Adenovirus Serotype 5 Packaged by Serotype 3 Hexon. J. Virol. Dec. 2002;76(24):12775-12782.
Xin et al., Prime-boost vaccination with plasmid DNA and a chimeric adenovirus type 5 vector with type 35 fiber induces protective immunity against HIV. Gene Ther. Dec. 2005;12(24):1769-1777.
Yamanaka, Alphavirus vectors for cancer gene therapy (Review). Int J Oncol. Apr. 2004;24(4):919-923.
Zhou et al., Development of a Complementing Cell Line and a System for Construction of Adenovirus Vectors with E1 and E2a Deleted. J Virol. Oct. 1996;70(10):7030-7038.
Zhou et al., Production of helper-dependent adenovirus vector relies on helper virus structure and complementing. J Gene Med. Sep.-Oct. 2002;4(5):498-509.
Zibert et al., Herpes simplex virus type-1 amplicon vectors for vaccine generation in acute lymphoblastic leukemia. Gene Ther. Dec. 2005;12(23):1707-1717.
Extended European Search Report issued in EP 11841347.5 dated Mar. 12, 2014.
Angelakopoulos et al., Safety and Shedding of an Attenuated Strain of Listeria monocytogenes with a Deletion of actA/plcB in Adult Volunteers: a Dose Escalation Study of oral Inoculation. Infect Immun. Jul. 2002:70(7):3592-3601.
Arlen et al., Strategies for the development of PSA-based vaccines for the treatment of advanced prostate cancer. Expert Rev Vaccines Aug. 2003;2(4):483-493.
Arlen et al. Pox viral vaccine approaches. Semin Oncol. Dec. 2005;32(6):549-555.
Arnold et al., Chimeric rhinoviruses as tools for vaccine development and characterization of protein epitopes. Intervirology 1996;39(1-2):72-78.
Arslan et al., A new approach to sequence comparison; normalized sequence alignment. Bioinformatics. Apr. 2001;17(4):327-337.
Atkins et al., Alphaviruses and their derived vectors as anti-tumor agents. Curr Cancer Drug Targets Nov. 2004;4(7):597-607.
Auerbuch et al., Development of a Competitive Index Assay to Evaluate the Virulence of Listeria monocytogenes actAMutants during Primary and Secondary Infection of Mice. Infect Immun. Sep. 2001;69(9):5953-5957.

(56) References Cited

OTHER PUBLICATIONS

Baez-Astua et al., Low-Dose Adenovirus Vaccine Encoding Chimeric Hepatitis B Virus Surface Antigen-Human Papillomavirus Type 16 E7 Proteins Induces Enhanced E7-Specific Antibody and Cytotoxic T-Cell Responses. J Virol. Oct. 2005;79(20):12807-12817.
Balasuriya et al., Expression of the Two Major Envelope Proteins of Equine Arteritis Virus as a Heterodimer is Necessary for Induction of Neutralizing Antibodies in Mice Immunized with Recombinant Venezuelan Equine Encephalitis Virus Replicon Particles. J Virol. Nov. 2000;74(22):10623-10630.
Baldwin et al., Vaccinia-Expressed Human Papillomavirus 16 and 18 E6 and E7 as a Therapeutic Vaccination for Vulval and Vaginal Intraepithelial Neoplasia. Clin Cancer Res. Nov. 1, 2003;9(14):5205-5213.
Bishop and Hinrichs, Adoptive transfer of immunity to Listeria monocytogenes. The influence of in vitro stimulation on lymphocyte subset requirements. J Immunol. Sep. 15, 1987;139(6):2005-2009.
Borrello and Pardoll., GM-CSF-based cellular vaccines: a review of the clinical experience. Cytokine Growth Factor Rev. Apr. 2002;13(2):185-193.
Briones et al., In Vivo Antitumor Effect of CD40L-transduced Tumor Cells as a Vaccine for B-Cell Lymphoma. Cancer Res. Jun. 1, 2002;62(11):3195-3199.
Brockstedt et al. Listeria-based cancer vaccines that segregate immunogenicity from toxicity. Proc Natl Acad Sci U S A. Sep. 21, 2004;101(38):13832-13837.
Casimiro et al., Attenuation of Simian Immunodeficiency Virus SIVmac239 Infection by Prophylactic Immunization with DNA and Recombinant Adenoviral Vaccine Vectors Expressing Gag. J Virol. Dec. 2005;79(24):15547-15555.
Cassetti et al., Antitumor efficacy of Venezuelan equine encephalitis virus replicon particles encoding mutated HPV16 E6 and E7 genes. Vaccine Jan. 2, 2004;22(3-4):520-527.
Cerundolo et al., Dendritic cells: a journey from laboratory to clinic. Nature Immunol. Jan. 2004;5(1):7-10.
Cheng et al., Cancer Immunotherapy Using Sindbis Virus Replicon Particles Encoding a VP22-Antigen Fusion. Hum Gene Ther. Mar. 1, 2002;13(4):553-568.
Creighton et al., Mechanisms and catalysts of disulfide bond formation in proteins. Trends Biotechnol. Jan. 1995;13(1):18-23.
DaSilva et al., Heterologous boosting increases immunogenicity of chimeric papillomavirus virus-like particle vaccines. Vaccine Jul. 4, 2003;21(23):3219-3227.
Dean, Epidermal deliver of protein an DNA vaccines. Expert Opin Drug Deliv. Mar. 2005;2(2):227-236.
Dela Cruz et al., Protein vaccination with the HER2/neu extracellular domain plus anti-HER2/neu antibody-cytokine fusion proteins induces a protective anti-HER2/neu immune response in mice. Vaccine Mar. 28, 2003;21 (13-14):1317-1326.
DePolo et al., VSV-G Pseudotyped Lentiviral Vector Particles Produced in Human Cells Are Inactivated by Human Serum Mol Ther. Sep. 2000;2(3):218-222.
Dinicola et al., Boosting T Cell-Mediated Immunity to Tyrosinase by Vaccinia Virus-Transduced, CD34+-Derived Dendritic Cell Vaccination: A Phase I Trial in Metastatic Melanoma. Clin Cancer Res. Aug. 15, 2004;10(16):5381-5390.
Disis et al., Peptide-Based, but Not Whole Protein, Vaccines Elicit Immunity to HER-2/neu, an Oncogenic Self-Protein. J Imnmunol. May 1, 1996;156(9):3151-3158.
Dollenmaier et al., Membrane-Associated Respiratory Syncytial Virus F Protein Expressed from a Human Rhinovirus Type 14 Vector is Immunogenic. Virology Mar. 15, 2001;281(2):216-230.
Donnelly et al., DNA Vaccines. Ann Rev Immunol. 1997;15:617-648.
Dranoff, GM-CSF-based cancer vaccines, Immunol. Rev. Oct. 2002;188:47-154.
Esslinger, et al., In vivo administration of a lentiviral vaccine targets DCs and induces efficient CD8+ T cell responses. J Clin Invest. Jun. 2003;111(11):1673-1681.

Estcourt et al., DNA vaccines against human immunodeficiency virus type 1. Immunol Rev. Jun. 2004;199:144-155.
Excler, Potentials and limitations of protein vaccines in infants. Vaccine Aug.-Sep. 1998;16(14-15):1439-1443.
Fensterle et al., Effective DNA Vaccination Against Listeriosis by Prime/Boost Inoculation with the Gene Gun. J Immunol. Oct. 15, 1999;163(8):4510-4518.
Ferreira et al., Use of adenoviral vectors as veterinary vaccines. Gene Ther. Oct. 2005;12 Suppl. 1:S73-S83.
Friese et al., MICA/NKG2D-Mediated Immunogene Therapy of Experimental Gliomas. Cancer Res. Dec. 15, 2003;63(24):8996-9006.
Gabrilovich, Dendritic cell vaccines for cancer treatment. Curr Opin Mel Ther. Oct. 2002;4(5):452-458.
Gaillard et al., Entry of L. monocytogenes into Cells is Mediated by Internalin, a Repeat Protein Reminiscent of Surface Antigens from Gram-Positive Cocci. Cell. Jun. 28, 1991;65(7):1127-1141.
Geiger et al., A generic RNA-pulsed dendritic cell vaccine strategy for renal cell Carcinoma. J Transl Med. Jul. 2005 26;3:29.
Gherardi et al., Towards a new generation of vaccines: the cytokine IL-12 as an adjuvant to enhance celluar immune responses to pathogens during prime-booster vaccination regimens. Histol Histopathol. Apr. 2001;16(2):655-667.
Goldberg et al., Comparison of Two Cancer Vaccines Targeting Tyrosinase: Plasmid DNA and Recombinant Alphavirus Replicon Particles. Clin. Cancer Res. Nov. 15, 2005; 11(22):8114-8121.
Greiner et al., Vaccine-based Therapy Directed against Carcinoembryonic Antigen Demonstrates Antitumor Activity on Spontaneous Intestinal Tumors in the Absence of Autoimmunity. Cancer Res. Dec. 1, 2002;62(23):6944-6951.
Groth and Calos, Phage integrases, biology and applications. J Mol Biol. Jan. 16, 2004;335(3):667-678.
Gunn et al., Two Listeria monocytogenes Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16. J Immunol. Dec. 1, 2001;167(11):6471-6479.
Hellebrand et al., Epstein-Barr virus vector-mediated gene transfer into human B cells: potential for antitumor vaccination. Gene Ther. Jan. 2006;13(2):150-162.
Hertoghs et al., Use of locked nucleic acid oligonucleotides to add functionality to plasmid DNA. Nucleic Acids Res. Oct. 15, 2003;31(20)5817-5830.
Hirschowitz et al., Autologous Dendritic Cell Vaccines for Non-Small-Cell Lung Cancer. J Clin Oncol. Jul. 15, 2004;22(14):2808-2815.
Hodge et al., Diversified prime and boost protocols using recombinant vaccinia virus and recombinant non-replicating avian pox virus to enhance T-cell immunity and antitumor responses. Vaccine Apr.-May 1997;15(6-7):759-768.
Howard et al., Differentiation of Listeria monocytogenes, Listeria innocua, Listeria ivanovii, and Listeria seeligeri by pulsed-field gel electrophoresis. Appl Environ Microbiol. Feb. 1992;58(2):709-712.
Hwang and Sanda, Prospects and limitations of recombinant poxviruses for prostate cancer immunotherapy. Curr Opin Mol Ther. Aug. 1999;1(4):471-479.
Johansen et al., Technological considerations related to the up-scaling of protein microencapsulation by spray-drying. Eur J Pharm Biopharm. Nov. 2000;50(3):413-417.
Johnson et al., Natural Atypical Listeria innocua Strains with Listeria monocytogenes Pathogenicity Island 1 Genes. Appl Environ Microbiol. Jul. 2004;70(7):4256-4266.
Johnston et al., Vaccination of macaques with SIV immunogens delivered by Venezuelan equine encephalitis virus replicon particle vectors followed by a mucosal challenge with SIVsmE660. Vaccine Oct. 10, 2005;23(42):4969-4979.
Jones and Portnoy, Characterization of Listeria monocytogenes pathogenesis in a strain expressing perfringoiysin O in place of listeriolysin O. Infect Immun. Dec. 1994;62(12):5608-5613.
Kann and Goldstein, Performance Evaluation of a New Algorithm for the Detection of Remote Homologs With Sequence Comparison. Proteins. Aug. 1, 2002;48(2)367-376.

(56) References Cited

OTHER PUBLICATIONS

Kao et al., Superior efficacy of dendritic cell-tumor fusion vaccine compared with tumor lysate-pulsed dendritic cell vaccine in colon cancer. Immunol Lett. Nov. 15, 2005;101(2):154-159.
Kaufman, Integrating Bench With Bedside: The Role of Vaccine Therapy in the Treatment of Solid Tumors. J Clin Oncol. Feb. 1, 2005;23(4)659-661.
Kaufman et al., Phase II Randomized Study of Vaccine Treatment of Advanced Prostate Cancer (E7897): A Trial of the Eastern Cooperative Oncology Group. J Clin Oncol. Jun. 1, 2004;22(11):2122-2132.
Kaufman et al. Targeting the local tumor microenvironment with vaccinia virus expressing B7. 1 for the treatment of melanoma. J Clin Invest. Jul. 2005;115(7):1903-1912.
Kikuchi et al., Inhibition of Orthotopic Human Bladder Tumor Growth by Lentiviral Gene Transfer of Endostatin. Clin Cancer Res. Mar. 1, 2004;10(5):1835-1842.
Kim et al., DNA Vaccines Employing Intracelluar Targeting Strategies and a Strategy to Prolong Dendritic Cell Life Generate a Higher Number of CD8+ Memory T Cells and Better Long-Term Antitumor Effects Compared with a DNA Prime-Vaccinia Boost Regimen. Hum Gen Ther. Jan. 2005;16(1):26-34.
Kim et al., Induction of Therapeutic Antitumor Immunity by in Vivo Administration of a Lentiviral Vaccine. Hum Gene Ther. Nov. 2005;16(11):1255-1266.
Kjaergaard et al., Active immunotherapy for advanced intracranial murine tumors by using dendritic cell-tumor cell fusion vaccines. J Neurosurg. Jul. 2005;103(1):156-164.
Koido et al., Assessment of fusion cells from patient-derived ovarian carcinoma cells and dendritic cells as a vaccine for clinical use. Gynecol Oncol. Nov. 2005;99(2):462-471.
Kudo-Saito et al., Intratumoral Vaccination and Diversified Subcutaneous/Intratumoral Vaccination with Recombinant Poxviruses Encoding a Tumor Antigen and Multiple Costimulatory Molecules. Clin Cancer Res. Feb. 1, 2004;10(3):1090-1099.
Kutzler and Weiner, Developing DNA vaccines that call to dendritic cells. J Clin Invest. Nov. 2004;114(9):1241-1244.
Kyte and Doolittle, A Simple Method for Displaying the Hydropathic Character of a Protein. J Mol Biol. May 5, 1982;157(1):105-132.
Lauer et al., Constitutive Activation of the PrfA Regulon Enhances the Potency of Vaccines Based on Live-Attenuated and Killed but Metabolically Active Listeria monocytogenes Strains. Infect Immun. Aug. 2008;76(8):3742-3753.
Lauer et al., Construction, Characterization, and Use of Two Listeria monocytogenes Site-Specific Phage Integration Vectors. J Bacteriol. Aug. 2002;184(15):4177-4186.
Lauterbach et al., Reduced immune responses after vaccination with a recombinant herpes simplex virus type 1 vector in the presence of antiviral immunity, J Gen Virol. Sep. 2005;86(Pt 9):2401-2410.
Leroux-Roels et al., Prevention of hepatitis B infections: vaccination and its limitations, Acta Clin Belg. Jul.-Aug. 2001;56(4):209-219.
Liao et al., Fusion Protein Vaccine by Domains of Bacterial Exotoxin Linked with a Tumor Antigen Generates Potent Immunologic Responses and Antitumor Effects. Cancer Res. Oct. 1, 2005;65(19):9089-9098.
Liau et al., Tumor Immunity within the Central Nervous System Stimulated by Recombinant Listeria monocytogenes Vaccination. Cancer Res. Apr. 15, 2002;62(8):2287-2293.
Lin et al., Boosting with Recombinant Vaccinia Increases HPV-16 E7-Specific T Cell Precursor Frequencies and Antitumor Effects of HPV-16 E7-Expressing Sindbis Virus Replicon Particles. Mol Ther. Oct. 2003;8(4):559-566.
Lingnau et al., Expression of the Listeria monocytogenes EGD inIA and inIB genes, whose products mediate bacterial entry into tissue culture cell lines, by PrfA-dependent and -independent mechanisms. Infect Immun. Oct. 1995;63(10):3896-3903.
Lundstrom, Alphavirus vectors for vaccine production and gene therapy. Expert Rev Vaccines Jun. 2003;2(3):447-459.
Luo et al., In vitro transcription of the Listeria monocytogenes virulence genes inIC and mpl reveals overlapping PrfA-dependent and -independent promoters that are differentially activated by GTP. Mol Miciobiol. Apr. 2004;52(1):39-52.
Mackova et al., Prime/boost immunotherapy of HPV16-induced tumors with E7 protein delivered by Bordetella adenylate cyclase and modified vaccinia virus Ankara Cancer Immunol Immunother. Jan. 2006;55(1):39-46.
Malowany et al., Development of Cell-Based Tuberculosis Vaccines: Genetically Modified Dendritic Cell Vaccine is a Much More Potent Activator of CD4 and CD8 T Cells Than Peptide- or Protein-Loaded Counterparts. Mol Ther. Apr. 2006;13(4):766-775.
Marshall et al., Phase I Study of Sequential Vaccinations With Fowlpox-CEA(6D)-TRICOM Alone and Sequentially With Vaccinia-CEA(6D)-TRICOM, With and Without Granulocyte-Macrophage Colony-Stimulating Factor, in Patients With Carcinoembryonic Antigen-Expressing Carcinomas. J Clin Oncol. Feb. 2005 123:720-731.
Marth, Booster Policy for Adults. Biologicals. Jun. 1997;25(2):199-203.
Mascola, Vaccines: Engineering immune evasion. Nature May 11, 2006;441(7090):161-162.
McCabe et al., Minimal Determinant Expressed by a Recombinant Vaccinia Virus Elicits Therapeutic Antitumor Cytolytic T Lymphocyte Responses. Cancer Res. Apr. 15, 1995;55(8):1741-1747.
Meyer et al., A phase I vaccination study with tyrosinase in patients with stage II melanoma using recombinant modified vaccinia virus Ankara (MVA-hTyr). Cancer Immunol Immunother. May 2005;54(5):453-467.
Mincheff et al., In vivo transfection and/or cross-priming of dendritic cells following DNA and adenoviral immunizations for immunotherapy of cancer—changes in peripheral mononuclear subsets and intracellular IL-4 and IFN-gamma lymphokine profile. Crit Rev Oncol Hematol. Jul.-Aug. 2001;39(1-2):125-132.
Minev et al., Insertion Signal Sequence Fused to Minimal Peptides Elicits Specific CD8+ T-Cell Responses and Prolongs Survival of Thymoma-bearing Mice. Cancer Res. Aug. 1, 1994;54(15):4155-4161.
Morenweiser, Downstream processing of viral vectors and vaccines. Gene Ther. Oct. 2005;12 Suppl. 1: SI03-S110.
Morse and Lyerly, Dendritic cell-based approaches to cancer Immunotherapy. Expert Opin Investig Drugs Oct. 1998;7(10):1617-1627.
Morse and Lyerly, DNA and RNA Modified Dendritic Cell Vaccines World J Surg. Jul. 2002,26(7):819-825.
Morse et al., CEA loaded dendritic cell vaccines. Cancer Chemother Biol Response Modif. 2002;20:385-390.
Morse et al., HER2 dendritic cell vaccines. Clin Breast Cancer Feb. 2003:3 Suppl.4:S164-S172.
Mueller and Freitag, Pleiotropic Enhancement of Bacterial Pathogenesis Resulting from the Constitutive Activation of the Listeria monocytogenes Regulatory Factor PrfA. Infect Immun. Apr. 2005;73(4):1917-1926.
Mullthaler et al., In vitro transcription of PrfA-dependent and -independent genes of Listeria monocytogenes. Mol Microbiol. Oct. 2001;42(1):111-120.
Munsen and Rodbard, Ligand: A Versatile Computerized Approach for Characterization of Ligand-Binding Systems, Anal Biochem. Sep. 1, 1980;107(1):220-239.
Nishitani et al., Cytokine Gene Therapy for Cancer with Naked DNA. Mol Urol, 2000 Summer;4(2):47-50.
Nunes-Duby et al., Similarities and differences among 105 members of the Int family of site-specific recombinases. Nucleic Acids Res. Jan. 15, 1998:26(2):391-406.
O'Riordan et al., Listeria intracellular growth and virulence require host-derived lipoic acid. Science. Oct. 17, 2003;302(5644):462-464.
Paessler et al., Recombinant Sindbis/Venezuelan Equine Encephalitis Virus is Highly Attenuated and Immunogenic. J Virol. Sep. 2003;77(17):9278-9286.
Palmowski et al., Competition Between CTL Narrows the Immune Response Induced by Primes-Boost Vaccination Protocols. J Immunol. May 1, 2002;168(9):4391-4398.

(56) References Cited

OTHER PUBLICATIONS

Pan et al., Modulation of disease, T cell responses, and measles virus clearance in monkeys vaccinated with H-encoding alphavirus replicon particles. Proc. Natl Acad Sci. USA Aug. 16, 2005;102:11581-11588.

Ciesielski et al., Cellular antitumor immune response to a branched lysine multiple antigenic peptide containing epitopes of a common tumor-specific antigen in a rat glioma model. Cancer Immunol Immunother. Feb. 2005;54 (2):107-119.

Huebener et al., Vaccination with mini genes encoding for novel 'self' antigens are effective in DNA-vaccination against neuroblastoma. Cancer Lett. Jul. 18, 2003;197(1-2):211-217.

Wagner et al., Identification of HLA-A*0201 binding antigenic peptides derived from the HOM-MEL-40/SSX-2 antigen that stimulate CTL from patients with SSX-2 positive cancers. Am Assoc Cancer Res. Proceed Annual Meeting, Mar. 2002;43:606.

Office Action issued by SIPO in Chinese patent application No. 201180062129X dated Jun. 27, 2014.

* cited by examiner

Fig. 7

% EGFRvIII$_{26-33}$-specific (IFN-γ-producing cells within CD8+ T cell population)

copies of EGFRvIII$_{20-40}$ : 1x, 5x

METHODS AND COMPOSITIONS FOR INDUCING AN IMMUNE RESPONSE TO EGFRVIII

CROSS REFERENCE TO RELATED APPLICATIONS

The present invention is filed under 35 U.S.C. §371 as the U.S. national phase of International Application No. PCT/US2011/061164, filed Nov. 17, 2011, which designated the U.S. and claims priority from U.S. Provisional Patent Application No. 61/414,850, filed Nov. 17, 2010, which is hereby incorporated in its entirety, including all tables, figures and claims.

SEQUENCE LISTING

The instant application contains a Sequence Listing which has been submitted 17,408 bytes in size.

BACKGROUND OF THE INVENTION

The following discussion of the background of the invention is merely provided to aid the reader in understanding the invention and is not admitted to describe or constitute prior art to the present invention.

The EGFR3 gene (c-erbB-1) is often amplified and overexpressed in malignant human tissues. Frequently, this amplification is correlated with structural rearrangement of the gene, resulting in in-frame deletion-mutants deficient in the intracellular and transmembrane domains of wild-type c-erb-1. One class of deletion-mutant identified in some malignant gliomas and non-small cell lung carcinomas is referred to as EGFRvIII. EGFRvIII is a mutation in which amino acids 6-273 (in the extracellular domain, with residue 1 being the residue immediately following the signal sequence) are deleted, and a glycine is inserted between residues 5 and 274. The sequence of the N-terminal 10 residues of the EGFRvIII mutation is LEEKKGNYVV (SEQ ID NO: 1).

Patients with EGFRvIII expressing breast cancers have detectable humoral and cellular immune responses against this peptide, suggesting that it serves as an immunogenic neo-antigen. A 13 amino acid peptide from this junction (LEEKKGNYVVTDH; SEQ ID NO: 2), referred to as PEPvIII, has been used to vaccinate humans with EGFRvIII-expressing tumors. In a recently published study, PEPvIII conjugated to KLH was administered to newly diagnosed glioblastoma multiforme ("GBM") patients treated by gross total resection (>95%), radiation and temozolomide who had no radiographic evidence of progression. Humoral immune responses to EGFRvIII were observed in 6 of 14 immunized patients, while 3 of 17 showed a positive DTH response. The median overall survival for patients treated with vaccine and temozolomide was 26.0 months from the time of histologic diagnosis, versus 15.0 months for a matched cohort receiving only temozolomide. These encouraging results support the utility of EGFRvIII-expressing vaccines and suggest that a more potent vaccine, one that elicits a robust, durable and potent antigen-specific T cell response, could improve the magnitude and duration of the anti-EGFRvIII response.

*Listeria monocytogenes* is a gram-positive intracellular bacterium being explored for its utility as a vaccine vector. Infection with *L. monocytogenes* elicits a potent CD8+ T cell response, necessary for the killing of *L. monocytogenes*-infected cells and control of infection. Attenuation of *L. monocytogenes* improves the safety of the vector 100-1,000 fold while maintaining or enhancing its immunogenicity. The ease with which the vector can be genetically manipulated, together with the straightforward production methodologies make *L. monocytogenes* an attractive platform for cancer vaccines.

There remains a need in the art for compositions and methods for stimulating an effective immune response to of EGFRvIII-expressing maligancies.

BRIEF SUMMARY OF THE INVENTION

The present invention provides compositions and methods for delivery of a multimeric EGFRvIII antigen vaccine using a bacterium recombinantly encoding and expressing such antigens.

In a first aspect of the invention, the invention relates to methods of inducing a T-cell response against EGFRvIII in a subject. These method comprise administering to a subject a composition comprising a bacterium which expresses one or more immunogenic polypeptides, the amino acid sequence of which comprise a plurality (2, 3, 4, 5, or more copies) of EGFRvIII polypeptide sequences, the sequence of which each comprise EEKKGNYV (SEQ ID NO: 3). In certain embodiments, these EGFRvIII-derived sequences can comprise or consist of LEEKKGNYV (SEQ ID NO: 4), LEEKKGNYVVTDH (SEQ ID NO: 2), or PASRALEEKKGNYVVTDHGSC (SEQ ID NO: 5). As described hereinafter, most preferred are *L. monocytogenes* bacterium expressing the immunogenic polypeptide(s) described herein.

As also described herein, such methods can stimulate an immune response, including one or more of a humoral response and antigen-specific T cell (CD4+ and/or CD8+) response, in said subject to the recombinantly expressed EGFRvIII polypeptides. The ability of such polypeptides to generate a CD4+ and/or CD8+ T cell response may be confirmed by a variety of methods described in detail herein and that are well known in the art. Preferably, when delivered to the subject, the compositions of the present invention induce an increase in the serum concentration of one or more, and preferably each of, proteins selected from the group consisting of IL-12p70, IFN-γ, IL-6, TNF α, and MCP-1 at 24 hours following said delivery; and induce a CD4+ and/or CD8+ antigen-specific T cell response against EGFRvIII.

In a related aspect of the invention, the invention relates to compositions useful for inducing a T-cell response against EGFRvIII in a subject. Such compositions comprise a bacterium which comprises a nucleic acid molecule, the sequence of which encodes one or more immunogenic polypeptides, the amino acid sequence of which comprise a plurality (2, 3, 4, 5, or more copies) of EGFRvIII polypeptide sequences, the sequence of which each comprise EEKKGNYV (SEQ ID NO: 3). In certain embodiments, these EGFRvIII-derived sequences can comprise or consist of LEEKKGNYV (SEQ ID NO: 4), LEEKKGNYVVTDH (SEQ ID NO: 2), or PASRALEEKKGNYVVTDHGSC (SEQ ID NO: 5). As described hereinafter, most preferred are *L. monocytogenes* bacterium expressing the immunogenic polypeptide(s) described herein. In certain embodiments, the nucleic acid sequences encoding the EGFRvIII-derived sequences are codon optimized for expression in the desired bacterium.

In another related aspect, the invention relates to a isolated nucleic acid molecule, the sequence of which encodes one or more immunogenic polypeptides, the amino acid sequence of which comprise a plurality (2, 3, 4, 5, or more copies) of EGFRvIII polypeptide sequences, the sequence of which each comprise EEKKGNYV (SEQ ID NO: 3), or the corresponding polypeptides themselves. In certain embodiments, these EGFRvIII-derived sequences can comprise or consist of LEEKKGNYV (SEQ ID NO: 4), LEEKKGNYVVTDH (SEQ ID NO: 2), or PASRALEEKKGNYVVTDHGSC (SEQ ID NO: 5).

Methods for deriving appropriate immunogenic polypeptide sequences are described in detail hereinafter. In certain embodiments, at least two of the EGFRvIII polypeptide sequences are separated by a polypeptide linker which is configured to be processed by proteases present in the subject. By way of example, one EGFRvIII polypeptide sequence may be separated from an adjacent EGFR polypeptide sequence by a sequence which is configured to be cleaved by the proteasome. In certain embodiments, each EGFRvIII polypeptide sequence is flanked by (and thereby separated from adjacent EGFR polypeptide sequence(s)) a sequence which is configured to be cleaved by the proteasome. Suitable polypeptide sequences, and the nucleic acid sequences encoding them, are described in detail hereinafter.

In certain embodiments, the immunogenic polypeptide(s) comprise one or more "cleavable" amino acid sequences selected from the group consisting of ASKVL↓ADGSVK; ASKVA↓GDGSIK; LSKVL↓ADGSVK; LAKSL↓ADLAVK; ASVVA↓GIGSIA; GVEKI↓NAANKG; and DGSKKA↓GDGNKK (SEQ ID NOS: 6-12). In these sequences, the antigenic sequence is placed at the location indicated by the arrow, such that the "cleavable" amino acid sequence flanks the antigenic sequence. These sequences may be combined such that any sequence to the left of an arrow may be combined with any sequence to the right of an arrow to create a new flanking pair.

One may also create strings of these sequences such as ASKVL↓ADGSVKASKVA↓GDGSIKLSKVL↓ ADGSVKASKVA↓GDGSIKLSKVL↓ADGSVK (SEQ ID NO: 13), again in which the antigenic sequence is placed at the location indicated by the arrow. In an effort to improve clarity, this listing shows the first flanking sequence underlined, the second not underlined, the third underlined, the fourth not underlined, and the fifth underlined. Another example is ASKVL↓ADGSVKDGSKKA↓GDGNKK LSKVL↓ADGSVKDGSKKA↓GDGNKKLSKVL↓ ADGSVKDGSKKA↓GDGNKK (SEQ ID NO: 14). These sequences are exemplary in nature only. Suitable proteasomal cleavage motifs are described in detail in Toes et al., J. Exp. Med. 194: 1-12, 2001, which is hereby incorporated by reference in its entirety. See also, Lauer et al., Infect. Immun 76: 3742-53, 2008; and Sinnathamby et al., (J. Immunother. 32: 856-69, 2009.

A number of bacterial species have been developed for use as vaccines and can be used as a vaccine platform in present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. The present invention contemplates the use of attenuated, commensal, and/or killed but metabolically active bacterial strains as vaccine platforms. In preferred embodiments the bacterium is *Listeria monocytogenes* comprising a nucleic acid sequence encoding for expression by the bacterium of the EGFRvIII polypeptide sequences of the invention. This nucleic acid is most preferably integrated into the genome of the bacterium. Attenuated and killed but metabolically active forms of *Listeria monocytogenes* are particularly preferred, and *Listeria monocytogenes* harboring an attenuating mutation in actA and/or inlB is described hereinafter in preferred embodiments. While the present invention is described herein with regard to bacterial vectors, suitable agents for delivery of a target antigen include additional recombinant vectors, for example, viruses, and naked DNA.

The vaccine compositions described herein can be administered to a host, either alone or in combination with a pharmaceutically acceptable excipient, in an amount sufficient to induce an appropriate immune response to prevent or treat a malignancy associated with EGFRvIII expression. Preferred conditions selected to induce a T cell response in a subject comprise administering the vaccine platform intravenously to a subject; however, administration may be oral, intravenous, subcutaneous, dermal, intradermal, intramuscular, mucosal, parenteral, intraorgan, intralesional, intranasal, inhalation, intraocular, intravascular, intranodal, by scarification, rectal, intraperitoneal, or any one or combination of a variety of well-known routes of administration.

In certain preferred embodiments, after the subject has been administered an effective dose of a vaccine containing the immunogenic polypeptides to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost." Examples of such regimens are described hereinafter.

A preferred *Listeria monocytogenes* for use in the present invention comprises a mutation in the prfA gene which locks the expressed prfA transcription factor into a constitutively active state. For example, a PrfA* mutant (G155S) has been shown to enhance functional cellular immunity following a prime-boost intravenous or intramuscular immunization regimen.

In certain embodiments, the EGFRvIII polypeptide sequences of the present invention are expressed as a fusion protein comprising an in frame secretory signal sequence, thereby resulting in their secretion as soluble polypeptide(s) by the bacterium. Numerous exemplary signal sequences are known in the art for use in bacterial expression systems. In the case where the bacterium is *Listeria monocytogenes*, it is preferred that the secretory signal sequence is a *Listeria monocytogenes* signal sequence, most preferably the ActA signal sequence. Additional ActA or other linker amino acids may also be expressed fused to the immunogenic polypeptide(s). In preferred embodiments, one or more immunogenic polypeptide(s) are expressed as fusion protein(s) comprising an in frame ActA-N100 sequence (e.g., selected from the group consisting of SEQ ID NO: 37, 38 and 39) or an amino acid sequence having at least 90% sequence identity to said ActA-N100 sequence.

In preferred embodiments, the vaccine composition comprises a *Listeria monocytogenes* expressing a fusion protein comprising:

(a) an ActA-N100 sequence selected from the group consisting of SEQ ID NO: 37, 38 and 39, or an amino acid sequence having at least 90% sequence identity to such a ActA-N100 sequence;

(b) an amino acid sequence comprising a plurality (2, 3, 4, 5, or more copies) of EGFRvIII polypeptide sequences, the sequence of which each comprise EEKKGNYV (SEQ ID NO: 3); and (c) a linker amino acid sequence positioned between at least two of the EGFRvIII polypeptide sequences, wherein the linker amino acid sequence is configured for proteasomal cleavage, wherein the fusion protein is expressed from a nucleic acid sequence operably linked to a *Listeria monocytogenes* ActA promoter.

In another aspect, the present invention relates to a method of evaluating an EGFRvIII immune response in a mouse model system. These methods comprise immunizing a mouse with an EGFRvIII polypeptide, and assessing the resulting EGFRvIII-specific immune response by determining reactivity to a polypeptide, the sequence of which consists of EEKKGNYV.

As noted above, in certain embodiments the nucleic acid sequences encoding the antigenic polypeptide(s) are codon optimized for expression by the bacterium (e.g., *Listeria monocytogenes*). As described hereinafter, different organisms often display "codon bias"; that is, the degree to which a given codon encoding a particular amino acid appears in the genetic code varies significantly between organisms. In general, the more rare codons that a gene contains, the less likely it is that the heterologous protein will be expressed at a reasonable level within that specific host system. These levels become even lower if the rare codons appear in clusters or in the N-terminal portion of the protein. Replacing rare codons with others that more closely reflect the host system's codon bias without modifying the amino acid sequence can increase the levels of functional protein expression. Methods for codon optimization are described hereinafter.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE FIGURES

FIG. 7 depicts enhanced CD8+ T cell priming following immunization with recombinant *Listeria* expressing multiple copies of EGFRvIII20-40, relative to the single copy variant.

DETAILED DESCRIPTION OF THE INVENTION

Figure 1:
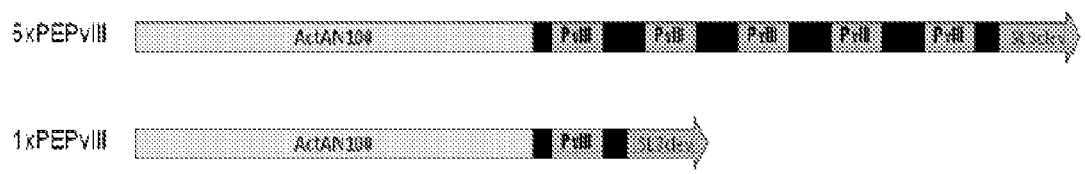
FIG. 1 schematically depicts exemplary expression cassettes for use in the present invention.

The present invention relates to compositions and methods for delivery of immunotherapy using a bacterium encoding and expressing a plurality of copies of an antigen derived from EGFRvIII.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

1. Definitions

Abbreviations used to indicate a mutation in a gene, or a mutation in a bacterium comprising the gene, are as follows. By way of example, the abbreviation "*L. monocytogenes* ΔactA" means that part, or all, of the actA gene was deleted. The delta symbol (Δ) means deletion. An abbreviation including a superscripted minus sign (*Listeria* ActA$^-$) means that the actA gene was mutated, e.g., by way of a deletion, point mutation, or frameshift mutation, but not limited to these types of mutations.

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses $CD34^+CD45RA^-$ early progenitor multipotent cells, $CD34^+CD45RA^+$ cells, $CD34^+CD45RA^+CD4^+$ $IL-3Ra^+$ pro-DC2 cells, $CD4^+$ $CD11c^-$ plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the $LD_{50}$, the rate of clearance from an organ, or the competitive index (see, e.g., Auerbuch, et al. (2001) Infect. Immunity 69:5953-5957). Generally, an attenuation results an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157:105-132).
(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe; and
(7) Small amino acids: Gly, Ala, Ser.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

An "extracellular fluid" encompasses, e.g., serum, plasma, blood, interstitial fluid, cerebrospinal fluid, secreted fluids, lymph, bile, sweat, fecal matter, and urine. An "extracellular fluid" can comprise a colloid or a suspension, e.g., whole blood or coagulated blood.

The term "fragments" in the context of polypeptides include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a larger polypeptide.

"Gene" refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, "gene" encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressable sequence is generally considered a pseudogene. The term gene also encompasses nucleic acid sequences encoding a ribonucleic acid such as rRNA, tRNA, or a ribozyme.

"Growth" of a bacterium such as *Listeria* encompasses, without limitation, functions of bacterial physiology and genes relating to colonization, replication, increase in protein content, and/or increase in lipid content. Unless specified otherwise explicitly or by context, growth of a *Listeria* encompasses growth of the bacterium outside a host cell, and also growth inside a host cell. Growth related genes include, without implying any limitation, those that mediate energy production (e.g., glycolysis, Krebs cycle, cytochromes), anabolism and/or catabolism of amino acids, sugars, lipids, minerals, purines, and pyrimidines, nutrient transport, transcription, translation, and/or replication. In some embodiments, "growth" of a *Listeria* bacterium refers to intracellular growth of the *Listeria* bacterium, that is, growth inside a host cell such as a mammalian cell. While intracellular growth of a *Listeria* bacterium can be measured by light microscopy or colony forming unit (CFU) assays, growth is not to be limited by any technique of measurement. Biochemical parameters such as the quantity of a *Listeria*1 antigen, *Listeria*1 nucleic acid sequence, or lipid specific to the *Listeria* bacterium, can be used to assess growth. In some embodiments, a gene that mediates growth is one that specifically mediates intracellular growth. In some embodiments, a gene that specifically mediates intracellular growth encompasses, but is not limited to, a gene where inactivation of the gene reduces the rate of intracellular growth but does not detectably, substantially, or appreciably, reduce the rate of extracellular growth (e.g., growth in broth), or a gene where inactivation of the gene reduces the rate of intracellular growth to a greater extent than it reduces the rate of extracellular growth. To provide a non-limiting example, in some embodiments, a gene where inactivation reduces the rate of intracellular growth to a greater extent than extracellular growth encompasses the situation where inactivation reduces intracellular growth to less than 50% the normal or maximal value, but reduces extracellular growth to only 1-5%, 5-10%, or 10-15% the maximal value. The invention, in certain aspects, encompasses a *Listeria* attenuated in intracellular growth but not attenuated in extracellular growth, a *Listeria* not attenuated in intracellular growth and not attenuated in extracellular growth, as well as a *Listeria* not attenuated in intracellular growth but attenuated in extracellular growth.

A "hydropathy analysis" refers to the analysis of a polypeptide sequence by the method of Kyte and Doolittle: "A Simple Method for Displaying the Hydropathic Character of a Protein". J. Mol. Biol. 157(1982)105-132. In this method, each amino acid is given a hydrophobicity score between 4.6 and −4.6. A score of 4.6 is the most hydrophobic and a score of −4.6 is the most hydrophilic. Then a window size is set. A window size is the number of amino acids whose hydrophobicity scores will be averaged and assigned to the first amino acid in the window. The calculation starts with the first window of amino acids and calculates the average of all the hydrophobicity scores in that window. Then the window moves down one amino acid and calculates the average of all the hydrophobicity scores in the second window. This pattern continues to the end of the protein, computing the average score for each window and assigning it to the first amino acid in the window. The averages are then plotted on a graph. The y axis represents the hydrophobicity scores and the x axis represents the window number. The following hydrophobicity scores are used for the 20 common amino acids.

| Arg: | −4.5 | Ser: | −0.8 | Lys: | −3.9 |
| Thr: | −0.7 | Asn: | −3.5 | Gly: | −0.4 |
| Asp: | −3.5 | Ala: | 1.8 | Gln: | −3.5 |
| Met: | 1.9 | Glu: | −3.5 | Cys: | 2.5 |
| His: | −3.2 | Phe: | 2.8 | Pro: | −1.6 |
| Leu: | 3.8 | Tyr: | −1.3 | Val: | 4.2 |
| Trp: | −0.9 | Ile: | 4.5 | | |

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Ligand" refers to a small molecule, peptide, polypeptide, or membrane associated or membrane-bound molecule, that is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

"Operably linked" in the context of a promoter and a nucleic acid encoding a mRNA means that the promoter can be used to initiate transcription of that nucleic acid.

The terms "percent sequence identity" and "% sequence identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090, 611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

"Spread" of a bacterium encompasses "cell to cell spread," that is, transmission of the bacterium from a first host cell to a second host cell, as mediated, for example, by a vesicle. Functions relating to spread include, but are not limited to, e.g., formation of an actin tail, formation of a pseudopod-like extension, and formation of a double-membraned vacuole.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have malignancy expressing EGFRvIII. In certain embodiments, the subject is suffering from a glioma (e.g., a GBM), a squamous cell carcinoma of the head and neck, a colorectal cancer, or a breast cancer.

The "target site" of a recombinase is the nucleic acid sequence or region that is recognized, bound, and/or acted upon by the recombinase (see, e.g., U.S. Pat. No. 6,379,943 issued to Graham, et al.; Smith and Thorpe (2002) Mol. Microbiol. 44:299-307; Groth and Calos (2004) J. Mol. Biol. 335:667-678; Nunes-Duby, et al. (1998) Nucleic Acids Res. 26:391-406).

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival.

"Vaccine" encompasses preventative vaccines. Vaccine also encompasses therapeutic vaccines, e.g., a vaccine administered to a mammal that comprises a condition or disorder associated with the antigen or epitope provided by the vaccine.

2. Exemplary EGFRvIII Antigens

The EGFRvIII antigen can comprise a sequence encoding at least one MHC class I epitope and/or at least one MHC class II epitope. The predictive algorithm "BIMAS" ranks potential HLA binding epitopes according to the predictive half-time disassociation of peptide/HLA complexes. The "SYFPEITHI" algorithm ranks peptides according to a score that accounts for the presence of primary and secondary HLA-binding anchor residues. Both computerized algorithms score candidate epitopes based on amino acid sequences within a given protein that have similar binding motifs to previously published HLA binding epitopes. Other algorithms can also be used to identify candidates for further biological testing.

As noted above, the EGFRvIII antigenic peptides of the present invention comprise a plurality (2, 3, 4, 5, or more copies) of EGFRvIII polypeptide sequences, the sequence of which each comprise EEKKGNYV (SEQ ID NO: 3). This sequence represents an H2-Kk-restricted epitope. A preferred EGFRvIII sequence comprises a plurality of copies of the sequence PASRALEEKKGNYVVTDHGSC (SEQ ID NO: 4), referred to herein as EGFRvIII$_{20-40}$. This 21-AA sequence overlaps the novel junction created by the 267-AA deletion relative to native EGFR. This also increases the chance of finding a class I-binding epitope that includes the novel glycine at the EGFRvIII splice site (45 unique 7 to 11-AA neopeptides within EGFRvIII$_{20-40}$ versus 22 potential class I-binding peptides in PEPvIII), while not including excessive amounts of native EGFR sequence. In addition, this expanded EGFRvIII peptide increases the number of potential class II-binding epitopes (30 neo-peptides >9-AA in EGFRvIII$_{20-40}$ versus 11 in PEPvIII) although vaccine potency is not necessarily dependent upon the presence of EGFRvIII-specific class II restricted epitopes.

As described hereinafter, antigen dosage is a critical determinate of vaccine potency. In order to maximize the number of EGFRvIII peptide-MHC complexes after vaccination, it is preferred that at least 5 copies of the EGFRvIII polypeptide sequence be included in a single protein construct, with each copy separated by a sequence predicted to facilitate proteasomal cleavage. As one example, such an amino acid sequence may be ASKVL<u>PASRALEEKKGNYVVTDHGSC</u>ADGSVKTSASKVA<u>PASRALEEKKGNYVVTDHGSC</u>GDGSIKLSKVL<u>PASRALEEKKGNYVVTDHGSC</u>ADGSVKASKVA<u>PASRALEEKKGNYVVTDHGSC</u>GDGSIKLSKVL<u>PASRALEEKKGNYVVTDHGSC</u>ADGS VKTS (SEQ ID NO: 15). For the sake of clarity, in this sequence the exemplary EGFRvIII-derived polypeptide sequences are underlined, and the exemplary "cleavable" sequences are not underlined.

By "immunogenic" as that term is used herein is meant that the antigen is capable of eliciting an antigen-specific humoral or T-cell response (CD4+ and/or CD8+). Selection of one or more antigens or derivatives thereof for use in the vaccine compositions of the present invention may be performed in a variety of ways, including an assessment of the ability of a bacterium of choice to successfully express and secrete the recombinant antigen(s); and/or the ability of the recombinant antigen(s) to initiate an antigen specific CD4+ and/or CD8+ T cell response. As discussed hereinafter, in order to arrive at a final selection of antigen(s) for use with a particular bacterial delivery vehicle, these attributes of the recombinant antigen(s) are preferably combined with the ability of the complete vaccine platform (meaning the selected bacterial expression system for the selected antigen(s)) to initiate both the innate immune response as well as an antigen-specific T cell response against the recombinantly expressed antigen(s). An initial determination of suitable antigens may be made by selecting antigen(s) or antigen fragment(s) that are successfully recombinantly expressed by the bacterial host of choice (e.g., Listeria), and that are immunogenic.

Direct detection of expression of the recombinant antigen by Western blot may be performed using an antibody that detects the antigenic sequence being recombinantly produced, or using an antibody that detects an included sequence (a "tag") which is expressed with the EGFRvIII-derived antigen as a fusion protein. For example, the antigen(s) may be expressed as fusions with an N-terminal portion of the Listeria ActA protein, and an anti-ActA antibody raised against a synthetic peptide (ATDSEDSSLNTDEWEEEK (SEQ ID NO:27)) corresponding to the mature N terminal 18 amino acids of ActA can be used to detect the expressed protein product.

Assays for testing the immunogenicity of antigens are described herein and are well known in the art. As an example, an antigen recombinantly produced by a bacterium of choice can be optionally constructed to contain the nucleotide sequence encoding an eight amino SIINFEKL (SEQ ID NO:28) peptide (also known as SL8 and ovalbumin$_{257-264}$), positioned in-frame at the carboxyl terminus of the antigen. Compositions such as the C-terminal SL8 epitope serve as a surrogate (i) to demonstrate that the recombinant antigen is being expressed in its entirety from N-terminal to C-terminal, and (ii) to demonstrate the ability of antigen presenting cells to present the recombinant antigen via the MHC class I pathway, using an in vitro antigen presentation assay. Such a presentation assay can be performed using the cloned C57BL/6-derived dendritic cell line DC2.4 together with the B3Z T cell hybridoma cell line as described hereinafter.

Alternatively, or in addition, immunogenicity may be tested using an ELISPOT assay as described hereinafter. ELISPOT assays were originally developed to enumerate B cells secreting antigen-specific antibodies, but have subsequently been adapted for various tasks, especially the identification and enumeration of cytokine-producing cells at the single cell level. Spleens may be harvested from animals inoculated with an appropriate bacterial vaccine, and the isolated splenocytes incubated overnight with or without peptides derived from the one or more EGFRvIII antigens expressed by the bacterial vaccine. An immobilized antibody captures any secreted IFN-γ, thus permitting subsequent measurement of secreted IFN-γ, and assessment of the immune response to the vaccine.

3. Recombinant Expression Systems—the "Vaccine Platform"

Selection of a vaccine platform for delivery of antigens is a critical component for an effective vaccine. Recombinant vectors are prepared using standard techniques known in the art, and contain suitable control elements operably linked to the nucleotide sequence encoding the target antigen. See, for example, Plotkin, et al. (eds.) (2003) Vaccines, 4$^{th}$ ed., W.B. Saunders, Co., Phila., Pa.; Sikora, et al. (eds.) (1996) Tumor Immunology Cambridge University Press, Cambridge, UK; Hackett and Ham (eds.) Vaccine Adjuvants, Humana Press, Totowa, N.J.; Isaacson (eds.) (1992) Recombinant DNA Vaccines, Marcel Dekker, NY, N.Y.; Morse, et al. (eds.) (2004) Handbook of Cancer Vaccines, Humana Press, Totowa, N.J.), Liao, et al. (2005) Cancer Res. 65:9089-9098; Dean (2005) Expert Opin. Drug Deliv. 2:227-236; Arlen, et al. (2003) Expert Rev. Vaccines 2:483-493; Dela Cruz, et al. (2003) Vaccine 21:1317-1326; Johansen, et al. (2000) Eur. J. Pharm. Biopharm. 50:413-417; Excler (1998) Vaccine 16:1439-1443; Disis, et al. (1996) J. Immunol. 156:3151-3158). Peptide vaccines are described (see, e.g., McCabe, et al. (1995) Cancer Res. 55:1741-1747; Minev, et al. (1994) Cancer Res. 54:4155-4161; Snyder, et al. (2004) J. Virology 78:7052-7060.

Suitable virus-derived antigen delivery vectors include viruses, modified viruses, and viral particles. The virus-derived vectors can be administered directly to a mammalian subject, or can be introduced ex vivo into an antigen presenting cell (APC), where the APC is then administered to the subject. Viral vectors may be based on, e.g., Togaviruses, including alphaviruses and flaviviruses; alphaviruses, such as Sindbis virus, Sindbis strain SAAR86, Semliki Forest virus (SFV), Venezuelan equine encephalitis (VEE), Eastern equine encephalitis (EEE), Western equine encephalitis, Ross River virus, Sagiyami virus, O'Nyong-nyong virus, Highlands J virus. Flaviviruses, such as Yellow fever virus, Yellow fever strain 17D, Japanese encephalitis, St. Louis encephalitis, Tick-borne encephalitis, Dengue virus, West Nile virus, Kunjin virus (subtype of West Nile virus); arterivirus such as equine arteritis virus; and rubivirus such as rubella virus, herpesvirus, modified vaccinia Ankara (MVA); avipox viral vector; fowlpox vector; vaccinia virus vector; influenza virus vector; adenoviral vector, human papilloma virus vector; bovine papilloma virus vector, and so on. Viral vectors may be based on an orthopoxvirus such as variola virus (smallpox), vaccinia virus (vaccine for smallpox), Ankara (MVA), or Copenhagen strain, camelpox, monkeypox, or cowpox. Viral vectors may be based on an avipoxvirus virus, such as fowlpox virus or canarypox virus.

Adenoviral vectors and adeno-associated virus vectors (AAV) are available, where adenoviral vectors include adenovirus serotype 5 (adeno5; Ad5), adeno6, adeno11, and adeno35. Available are at least 51 human adenovirus serotypes, classified into six subgroups (subgroups A, B, C, D, E, and F). Adenovirus proteins useful, for example, in assessing immune response to an "empty" advenoviral vector, include hexon protein, such as hexon 3 protein, fiber protein, and penton base proteins, and human immune responses to adenoviral proteins have been described (see, e.g., Wu, et al. (2002) J. Virol. 76:12775-12782; Mascola (2006) Nature 441:161-162; Roberts, et al. (2006) Nature 441:239-243). The following table describes exemplary virus-derived vaccine vectors for use in the present invention:

| | |
|---|---|
| Adenoviral vectors and adeno-associated virus vectors (AAV). | Polo and Dubensky (2002) Drug Discovery Today 7: 719-727; Xin, et al. (2005) Gene Ther. 12: 1769-1777; Morenweiser (2005) Gene Ther. 12 (Suppl. 1) S103-S110; Casimiro, et al. (2005) J. Virol. 79: 15547-15555; Ferreira, et al. (2005) Gene Ther. 12 Suppl. 1: S73-S83; Baez-Astua, et al. (2005) J. Virol. 79: 12807-12817; Vanniasinkam and Ertl (2005) Curr. Gene Ther. 5: 203-212; Tatsis and Ertl (2004) Mol. Ther. 10: 616-629; Santosuosso, et al. (2005) Viral Immunol. 18: 283-291; Zhou, et al. (1996) J. Virol. 70: 7030-7038; Zhou, et al. (2002) J. Gene Med. 4: 498-509. |
| Vaccinia virus | Kim, et al. (2005) Hum. Gen. Ther. 16: 26-34; Kaufman, et al. (2005) J. Clin. Invest. 115: 1903-1912; Kaufman, et al. (2004) J. Clin. Oncol. 22: 2122-2132; Marshall, et al. (2005) J. Clin. Invest. 23: 720-731; Hwang and Sanda (1999) Curr. Opin. Mol. Ther. 1: 471-479; Baldwin, et al. (2003) Clin. Cancer Res. 9: 5205-5213; |
| Modified vaccinia Ankara (MVA) | Mackova, et al. (2006) Cancer Immunol. Immunother. 55: 39-46; Meyer, et al. (2005) Cancer Immunol. Immunother. 54: 453-467; Palmowski, et al. (2002) J. Immunol. 168: 4391-4398; |
| Vaccinia derivative NYVAC | Paoletti (1996) Proc. Natl. Acad. Sci. USA 93: 11349-11353; |
| Poxviruses, including avipox, e.g., fowlpox and canarypox | Kaufman (2005) J. Clin. Oncol. 23: 659-661; Kudo-Saito, et al. (2004) Clin. Cancer Res. 10: 1090-1099; Greiner, et al. (2002) Cancer Res. 62: 6944-6951; Marshall, et al. (2005) J. Clin. Invest. 23: 720-731; Hwang and Sanda (1999) Curr. Opin. Mol. Ther. 1: 471-479; Hodge, et al. (1997) Vaccine 15: 759-768; Skinner, et al. (2005) Expert Rev. Vaccines 4: 63-76; Rosenberg, et al. (2003) Clin. Cancer Res. 9: 2973-2980. |
| Antigen presenting cells transduced with a virus-derived vector. | Di Nicola, et al. (2004) Clin. Cancer Res. 10: 5381-5390; |
| Alphavirus-derived vectors, e.g., Sindbis virus, Semliki Forest virus, and Venezuelan equine encephalitis (VEE). | Polo and Dubensky (2002) Drug Discovery Today 7: 719-727; Polo, et al. (1999) Proc. Natl. Acad. Sci. USA 96: 4598-4603; Schlesinger (2001) Expert Opin. Biol. Ther. 1: 177-191; Pan, et al. (2005) Proc. Natl. Acad. Sci. USA 102: 11581-11588; Lundstrom (2003) Expert Rev. Vaccines 2: 447-459; Shafferman, et al. (1996) Adv. Exp. Med. Biol. 397: 41-47; Yamanaka (2004) Int. J. Oncol. 24: 919-923; Atkins, et al. (2004) Curr. Cancer Drug Targets 4: 597-607. |
| Chimeric virus-derived vectors, such as chimeric alphaviruses. | Sindbis virus/Venezualan equine encephalitis virus (SINV/VEEV) (see, e.g., Perri, et al. (2003) J. Virol. 77: 10394-10403; Paessler, et al. (2003) J. Virol. 77: 9278-9286). |
| Herpesviruses, including herpes simplex and Epstein-Barr virus-derived vectors | Hellebrand, et al. (2006) Gene Ther. 13: 150-162; Lauterbach, et al. (2005) J. Gen. Virol. 86: 2401-2410; Zibert, et al. (2005) Gene Ther. 12: 1707-1717; Thiry, et al. (2006) Vet. Microbiol. 113: 171-177; Trapp, et al. (2005) J. Virol. 79: 5445-5454. |

-continued

| | |
|---|---|
| Rhinoviruses | Dollenmaier, et al. (2001) Virology 281: 216-230; Arnold, et al. (1996) Intervirology 39: 72-78. |
| Lentiviruses | DePolo, et al. (2000) Mol. Ther. 2: 218-222; Pellinen, et al. (2004) Int. J. Oncol. 25: 1753-1762; Esslinger, et al. (2003) J. Clin. Invest. 111: 1673-1681; Kikuchi, et al. (2004) Clin. Cancer Res. 10: 1835-1842; Kim, et al. (2005) Hum. Gene Ther. 16: 1255-1266. |
| Viral particle vaccines | Polo and Dubensky (2002) Drug Discovery Today 7: 719-727; Cheng, et al. (2002) Hum. Gene Ther. 13: 553-568; Lin, et al. (2003) Mol. Ther. 8: 559-566; Balasuriya, et al. (2000) J. Virol. 74: 10623-10630; Goldberg, et al. (2005) Clin. Cancer Res. 11: 8114-8121; Johnston, et al. (2005) Vaccine 23: 4969-4979; Quinnan, et al. (2005) J. Virol. 79: 3358-3369; Cassetti, et al. (2004) Vaccine 22: 520-527; Williamson, et al. (2003) AIDS Res. Hum. Retroviruses 19: 133-144; Perri, et al. (2003) J. Virol. 77: 10394-10403; Da Silva, et al. (2003) Vaccine 21: 3219-3227; |

Antigen presenting cell (APC) vectors, such as a dendritic cell (DC) vector, include cells that are loaded with an antigen, loaded with a tumor lysate, or transfected with a composition comprising a nucleic acid, where the nucleic acid can be, e.g., a plasmid, mRNA, or virus. DC/tumor fusion vaccines may also be used. See, e.g., Di Nicola, et al. (2004) Clin. Cancer Res. 10:5381-5390; Cerundolo, et al. (2004) Nature Immunol. 5:7-10; Parmiani, et al. (2002) J. Natl. Cancer Inst. 94:805-818; Kao, et al. (2005) Immunol. Lett. 101:154-159; Geiger, et al. (2005) J. Transl. Med. 3:29; Osada, et al. (2005) Cancer Immunol. Immunother. Nov.5,1-10 [epub ahead of print]; Malowany, et al. (2005) Mol. Ther. 13:766-775; Morse and Lyerly (2002) World J. Surg. 26:819-825; Gabrilovich (2002) Curr. Opin. Mol. Ther. 4:454-458; Morse, et al. (2003) Clin. Breast Cancer 3 Suppl.4:S164-5172; Morse, et al. (2002) Cancer Chemother. Biol. Response Modif. 20:385-390; Arlen, et al. (2003) Expert Rev. Vaccines 2:483-493; Morse and Lyerly (1998) Expert Opin. Investig. Drugs 7:1617-1627; Hirschowitz, et al. (2004) J. Clin. Oncol. 22:2808-2815; Vasir, et al. (2005) Br. J. Haematol. 129:687-700; Koido, et al. (2005) Gynecol. Oncol. 99:462-471.

Tumor cells, for example, autologous and allogeneic tumor cells, are available as vaccines (Arlen, et al. (2005) Semin Oncol. 32:549-555). A vaccine may also comprise a modified tumor cell, for example, a tumor cell lysate, or an irradiated tumor cell. The tumor cell can also be modified by incorporating a nucleic acid encoding an molecule such as a cytokine (GM-CSF, IL-12, IL-15, and the like), a NKG2D ligand, CD40L, CD80, CD86, and the like (see, e.g., Dranoff (2002) Immunol. Rev. 188:147-154; Jain, et al. (2003) Ann. Surg. Oncol. 10:810-820; Borrello and Pardoll (2002) Cytokine Growth Factor Rev. 13:185-193; Chen, et al. (2005) Cancer Immunol. Immunother. 27:1-11; Kjaergaard, et al. (2005) J. Neurosurg. 103:156-164; Tai, et al. (2004) J. Biomed. Sci. 11:228-238; Schwaab, et al. (2004) J. Urol. 171:1036-1042; Friese, et al. (2003) Cancer Res. 63:8996-9006; Briones, et al. (2002) Cancer Res. 62:3195-3199; Vieweg and Dannull (2003) Urol. Clin. North Am. 30:633-643; Mincheff, et al. (2001) Crit. Rev. Oncol. Hematol. 39:125-132).

Antigen expression platforms may also be provided using naked DNA vectors and naked RNA vectors. These vaccines containing nucleic acids may be administered by a gene gun, electroporation, bacterial ghosts, microspheres, microparticles, liposomes, polycationic nanoparticles, and the like (see, e.g., Donnelly, et al. (1997) Ann Rev. Immunol. 15:617-648; Mincheff, et al. (2001) Crit. Rev. Oncol. Hematol. 39:125-132; Song, et al. (2005) J. Virol. 79:9854-9861; Estcourt, et al. (2004) Immunol. Rev. 199:144-155). Reagents and methodologies for administration of naked nucleic acids, e.g., by way of a gene gun, intradermic, intramuscular, and electroporation methods, are available. The nucleic acid vaccines may comprise a locked nucleic acid (LNA), where the LNA allows for attachment of a functional moiety to the plasmid DNA, and where the functional moiety can be an adjuvant (see, e.g., Fensterle, et al. (1999) J. Immunol. 163: 4510-4518; Strugnell, et al. (1997) Immunol. Cell Biol. 75:364-369; Hertoughs, et al. (2003) Nucleic Acids Res. 31:5817-5830; Trimble, et al. (2003) Vaccine 21:4036-4042; Nishitani, et al. (2000) Mol. Urol. 4:47-50; Tuting (1999) Curr. Opin. Mol. Ther. 1:216-225). Nucleic acid vaccines can be used in combination with reagents that promote migration of immature dendritic cells towards the vaccine, and a reagent that promotes migration of mature DCs to the draining lymph node where priming can occur, where these reagents encompass MIP-1alpha and Flt3L (see, e.g., Kutzler and Weiner (2004) J. Clin. Invest. 114:1241-1244; Sumida, et al. (2004) J. Clin. Invest. 114:1334-1342).

A number of bacterial species have been developed for use as vaccines and can be used in the present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. See, e.g., WO04/006837; WO07/103225; and WO07/117371, each of which is hereby incorporated by reference in its entirety, including all tables, figures, and claims. The bacterial vector used in the vaccine composition may be a facultative, intracellular bacterial vector. The bacterium may be used to deliver a polypeptide described herein to antigen-presenting cells in the host organism. As described herein, *L. monocytogenes* provides a preferred vaccine platform for expression of the antigens of the present invention.

Both attenuated and commensal microorganisms have been successfully used as carriers for vaccine antigens, but bacterial carriers for the antigens are optionally attenuated or killed but metabolically active (KBMA). The genetic background of the carrier strain used in the formulation, the type of mutation selected to achieve attenuation, and the intrinsic properties of the immunogen can be adjusted to optimize the extent and quality of the immune response elicited. The general factors to be considered to optimize the immune response stimulated by the bacterial carrier include: selection of the carrier; the specific background strain, the attenuating mutation and the level of attenuation; the stabilization of the attenuated phenotype and the establishment of the optimal dosage. Other antigen-related factors to consider include: intrinsic properties of the antigen; the expression system; antigen-display form and stabilization of the recombinant phenotype; co-expression of modulating molecules and vaccination schedules.

A preferred feature of the vaccine platform is the ability to initiate both the innate immune response as well as an antigen-specific T cell response against the recombinantly expressed antigen(s). For example, L. monocytogenes expressing the antigen(s) described herein can induce intrahepatic Type 1 interferon (IFN-α/β) and a downstream cascade of chemokines and cytokines. In response to this intrahepatic immune stimulation, NK cells and antigen presenting cells (APCs) are recruited to the liver. In certain embodiments, the vaccine platform of the present invention induces an increase at 24 hours following delivery of the vaccine platform to the subject in the serum concentration of one or more, and preferably all, cytokines and chemokines selected from the group consisting of IL-12p70, IFN-γ, IL-6, TNF α, and MCP-1; and induces a CD4+ and/or CD8+ antigen-specific T cell response against one or more EGFRvIII-derived antigens expressed by the vaccine platform. In other embodiments, the vaccine platform of the present invention also induces the maturation of resident immature liver NK cells as demonstrated by the upregulation of activation markers such as DX5, CD11b, and CD43 in a mouse model system, or by NK cell-mediated cytolytic activity measured using $^{51}$Cr-labeled YAC-1 cells that were used as target cells.

In various embodiments, the vaccines and immunogenic compositions of the present invention can comprise Listeria monocytogenes configured to express the desired EGFRvIII-derived antigen(s). The ability of L. monocytogenes to serve as a vaccine vector has been reviewed in Wesikirch, et al., Immunol. Rev. 158:159-169 (1997). A number of desirable features of the natural biology of L. monocytogenes make it an attractive platform for application to a therapeutic vaccine. The central rationale is that the intracellular lifecycle of L. monocytogenes enables effective stimulation of CD4+ and CD8+ T cell immunity. Multiple pathogen associated molecular pattern (PAMP) receptors including TLRs (TLR2, TLR5, TLR9) and nucleotide-binding oligomerization domains (NOD) are triggered in response to interaction with L. monocytogenes macromolecules upon infection, resulting in the pan-activation of innate immune effectors and release of Th-1 polarizing cytokines, exerting a profound impact on the development of a CD4+ and CD8+ T cell response against the expressed antigens.

Strains of L. monocytogenes have recently been developed as effective intracellular delivery vehicles of heterologous proteins providing delivery of antigens to the immune system to induce an immune response to clinical conditions that do not permit injection of the disease-causing agent, such as cancer and HIV. See, e.g., U.S. Pat. No. 6,051,237; Gunn et al., J. Immunol., 167:6471-6479 (2001); Liau, et al., Cancer Research, 62: 2287-2293 (2002); U.S. Pat. No. 6,099,848; WO 99/25376; WO 96/14087; and U.S. Pat. No. 5,830,702), each of which is hereby incorporated by reference in its entirety, including all tables, figures, and claims. A recombinant L. monocytogenes vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995).

Attenuated and killed but metabolically active forms of L. monocytogenes useful in immunogenic compositions have been produced. WO07/103225; and WO07/117371), each of which is hereby incorporated by reference in its entirety, including all tables, figures, and claims. The ActA protein of L. monocytogenes is sufficient to promote the actin recruitment and polymerization events responsible for intracellular movement. A human safety study has reported that oral administration of an actA/plcB-deleted attenuated form of L. monocytogenes caused no serious sequelae in adults (Angelakopoulos et al., Infection and Immunity, 70:3592-3601 (2002)). Other types of attenuated forms of L. monocytogenes have also been described (see, for example, WO 99/25376 and U.S. Pat. No. 6,099,848, which describe auxotrophic, attenuated strains of Listeria that express heterologous antigens).

In certain embodiments, the L. monocytogenes used in the vaccine compositions of the present invention is a live-attenuated strain which comprises an attenuating mutation in actA and/or inlB, and preferably a deletion of all or a portion of actA and inlB (referred to herein as "Lm ΔactA/ΔinlB"), and contains recombinant DNA encoding for the expression of the EGFRvIII-derived antigen(s) of interest. The EGFRvIII-derived antigen(s) are preferably under the control of bacterial expression sequences and are stably integrated into the L. monocytogenes genome. Such a L. monocytogenes vaccine strain therefore employs no eukaryotic transcriptional or translational elements.

The invention also contemplates a Listeria attenuated in at least one regulatory factor, e.g., a promoter or a transcription factor. The following concerns promoters. ActA expression is regulated by two different promoters (Vazwuez-Boland, et al. (1992) Infect. Immun 60:219-230). Together, InlA and InlB expression is regulated by five promoters (Lingnau, et al. (1995) Infect. Immun 63:3896-3903). The transcription factor prfA is required for transcription of a number of L. monocytogenes genes, e.g., hly, plcA, ActA, mpl, prfA, and iap. PrfA's regulatory properties are mediated by, e.g., the PrfA-dependent promoter (PinlC) and the PrfA-box. The present invention, in certain embodiments, provides a nucleic acid encoding inactivated, mutated, or deleted in at least one of ActA promoter, inlB promoter, PrfA, PinlC, PrfA box, and the like (see, e.g., Lalic Mullthaler, et al. (2001) Mol. Microbiol. 42:111-120; Shetron-Rama, et al. (2003) Mol. Microbiol. 48:1537-1551; Luo, et al. (2004) Mol. Microbiol. 52:39-52). PrfA can be made constitutively active by a Gly145Ser mutation, Gly155Ser mutation, or Glu77Lys mutation (see, e.g., Mueller and Freitag (2005) Infect. Immun 73:1917-1926; Wong and Freitag (2004) J. Bacteriol. 186:6265-6276; Ripio, et al. (1997) J. Bacteriol. 179:1533-1540).

Attenuation can be effected by, e.g., heat-treatment or chemical modification. Attenuation can also be effected by genetic modification of a nucleic acid that modulates, e.g., metabolism, extracellular growth, or intracellular growth, genetic modification of a nucleic acid encoding a virulence factor, such as Listeria1 prfA, actA, listeriolysin (LLO), an adhesion mediating factor (e.g., an internalin such as inlA or inlB), mpl, phosphatidylcholine phospholipase C (PC-PLC), phosphatidylinositol-specific phospholipase C (PI PLC; plcA gene), any combination of the above, and the like. Attenuation can be assessed by comparing a biological function of an attenuated Listeria with the corresponding biological function shown by an appropriate parent Listeria.

The present invention, in other embodiments, provides a Listeria that is attenuated by treating with a nucleic acid targeting agent, such as a cross linking agent, a psoralen, a nitrogen mustard, cis platin, a bulky adduct, ultraviolet light, gamma irradiation, any combination thereof, and the like. Typically, the lesion produced by one molecule of cross linking agent involves cross linking of both strands of the double helix. The Listeria of the invention can also be attenuated by mutating at least one nucleic acid repair gene, e.g., uvrA, uvrB, uvrAB, uvrC, uvrD, uvrAB, phrA, and/or a gene mediating recombinational repair, e.g., recA. Moreover, the invention provides a Listeria attenuated by both a nucleic acid targeting agent and by mutating a nucleic acid repair gene. Additionally, the invention encompasses treating with a light sensitive nucleic acid targeting agent, such as a psoralen, and/or a light sensitive nucleic acid cross linking agent, such as psoralen, followed by exposure to ultraviolet light.

Attenuated Listeria useful in the present invention are described in, e.g., in U.S. Pat. Publ. Nos. 2004/0228877 and 2004/0197343, each of which is incorporated by reference herein in its entirety. Various assays for assessing whether a particular strain of Listeria has the desired attenuation are provided, e.g., in U.S. Pat. Publ. Nos. 2004/0228877, 2004/0197343, and 2005/0249748, each of which is incorporated by reference herein in its entirety.

In other embodiments, the L. monocytogenes used in the vaccine compositions of the present invention is a killed but metabolically active (KBMA) platform derived from Lm ΔactA/ΔinlB, and also is deleted of both uvrA and uvrB, genes encoding the DNA repair enzymes of the nucleotide excision repair (NER) pathway, and contains recombinant DNA encoding for the expression of the EGFRvIII-derived antigen(s) of interest. The antigen(s) of interest are preferably under the control of bacterial expression sequences and are stably integrated into the L. monocytogenes genome. The KBMA platform is exquisitely sensitive to photochemical inactivation by the combined treatment with the synthetic psoralen, S-59, and long-wave UV light. While killed, KBMA Lm vaccines can transiently express their gene products, allowing them to escape the phagolysosome and induce functional cellular immunity and protection against wild-typeWT Lm and vaccinia virus challenge.

In certain embodiments, an attenuated or KBMA L. monocytogenes vaccine strain comprise a constitutively active prfA gene (referred to herein as PrfA* mutants). PrfA is a transcription factor activated intracellularly which induces expression of virulence genes and encoded heterologous antigens (Ags) in appropriately engineered vaccine strains. As noted above, expression of the actA gene is responsive to PrfA, and the actA promoter is a PrfA responsive regulatory element. Inclusion of a prfA G155S allele can confer significant enhanced vaccine potency of live-attenuated or KBMA vaccines. Preferred PrfA mutants are described in U.S. Provisional patent application 61/054,454, entitled COMPOSITIONS COMPRISING PRFA* MUTANT LISTERIA AND METHODS OF USE THEREOF, filed May 19, 2008, which is hereby incorporated in its entirety including all tables, figures, and claims.

The sequence of L. monocytogenes PrfA, which includes a glycine at residue 155, is as follows (SEQ ID NO: 16):

```
MNAQAEEFKK YLETNGIKPK QFHKKELIFN QWDPQEYCIF       50
LYDGITKLTS

ISENGTIMNL QYYKGAFVIM SGFIDTETSV GYYNLEVISE      100
QATAYVIKIN

ELKELLSKNL THFFYVFQTL QKQVSYSLAK FNDFSINGKL      150
GSICGQLLIL

TYVYGKETPD GIKITLDNLT MQELGYSSGI AHSSAVSRII      200
SKLKQEKVIV

YKNSCFYVQN LDYLKRYAPK LDEWFYLACP ATWGKLN         237
```

The sequence of L. monocytogenes PrfA*, which includes a serine at residue 155, is as follows (SEQ ID NO: 17):

```
MNAQAEEFKK YLETNGIKPK QFHKKELIFN QWDPQEYCIF       50
LYDGITKLTS

ISENGTIMNL QYYKGAFVIM SGFIDTETSV GYYNLEVISE      100
QATAYVIKIN

ELKELLSKNL THFFYVFQTL QKQVSYSLAK FNDFSINGKL      150
GSICGQLLIL

TYVYSKETPD GIKITLDNLT MQELGYSSGI AHSSAVSRII      200
SKLKQEKVIV

YKNSCFYVQN LDYLKRYAPK LDEWFYLACP ATWGKLN         237
```

4. Antigenic Constructs

The antigenic construct expressed by the vaccine strain of the present invention comprises at a minimum a nucleic acid encoding a secretory sequence operable within the vaccine platform to support secretion, fused to the EGFRvIII-derived antigen(s) to be expressed. In the case of a bacterial platform, the resulting fusion protein is operably linked to regulatory sequences (e.g., a promoter) necessary for expression of the fusion protein by the bacterial vaccine platform. The present invention is not to be limited to polypeptide and peptide antigens that are secreted, but also embraces polypeptides and peptides that are not secreted or cannot be secreted from a Listeria or other bacterium. But preferably, the EGFRvIII-derived antigen(s) are expressed in a soluble, secreted form by a bacterial vaccine strain when the strain is inoculated into a recipient.

Table 1 discloses a number of non-limiting examples of signal peptides for use in fusing with a fusion protein partner sequence such as a heterologous antigen. Signal peptides tend to contain three domains: a positively charged N-terminus (1-5 residues long); a central hydrophobic comain (7-15 residues long); and a neutral but polar C-terminal domain.

TABLE 1

Bacterial signal pathway. Signal peptides are identified by the signal peptidase site.

| Signal peptidase site (cleavage site represented by ') | Gene | Genus/species |
|---|---|---|
| secA1 pathway | | |
| TEA'KD (SEQ ID NO: 18) | hly (LLO) | Listeria monocytogenes |
| VYA'DT (SEQ ID NO: 19) | Usp45 | Lactococcus lactis |
| IQA'EV (SEQ ID NO: 20) | pag | Bacillus anthracis |

TABLE 1-continued

Bacterial signal pathway. Signal peptides are identified by the signal peptidase site.

| Signal peptidase site (cleavage site represented by ') | Gene | Genus/species |
|---|---|---|
| | (protective antigen) | |
| secA2 pathway | | |
| ASA'ST (SEQ ID NO: 21) | iap (invasion-associated protein) p60 | Listeria monocytogenes |
| VGA'FG (SEQ ID NO: 22) | NamA lmo2691 (autolysin) | Listeria monocytogenes |
| AFA'ED (SEQ ID NO: 23) | * BA_0281 (NLP/P60 Family) | Bacillus anthracis |
| VQA'AE (SEQ ID NO: 24) | * atl (autolysin) | Staphylococcus aureus |
| Tat pathway | | |
| DKA'LT (SEQ ID NO: 25) | lmo0367 | Listeria monocytogenes |
| VGA'FG (SEQ ID NO: 26) | PhoD (alkaline phosphatase) | Bacillus subtillis |

* Bacterial autolysins secreted by sec pathway (not determined whether secA1 or secA2). Secretory sequences are encompassed by the indicated nucleic acids encoded by the Listeria EGD genome (GenBank Acc. No. NC_003210) at, e.g., nucleotides 45434-456936 (inlA); nucleotides 457021-457125 (inlB); nucleotides 1860200-1860295 (inlC); nucleotides 286219-287718 (inlE); nucleotides 205819-205893 (hly gene; LLO) (see also GenBank Acc. No. P13128); nucleotides 209470-209556 (ActA) (see also GenBank Acc. No. S20887).
The referenced nucleic acid sequences, and corresponding translated amino acid sequences, and the cited amino acid sequences, and the corresponding nucleic acid sequences associated with or cited in that reference, are incorporated by reference herein in their entirety.

In certain exemplary embodiments described hereinafter, the EGFRvIII-derived sequence(s) may be expressed as a single polypeptide fused to an amino-terminal portion of the L. monocytogenes ActA protein which permits expression and secretion of a fusion protein from the bacterium within the vaccinated host. In these embodiments, the antigenic construct may be a polynucleotide comprising a promoter operably linked to a nucleic acid sequence encoding a fusion protein, wherein the fusion protein comprises (a) modified ActA and (b) one or more EGFRvIII-derived epitopes to be expressed as a fusion protein following the modified ActA sequence.

By "modified ActA" is meant a contiguous portion of the L. monocytogenes ActA protein which comprises at least the ActA signal sequence, but does not comprise the entirety of the ActA sequence, or that has at least about 80% sequence identity, at least about 85% sequence identity, at least about 90% sequence identity, at least about 95% sequence identity, or at least about 98% sequence identity to such an ActA sequence. The ActA signal sequence is MGLNRFMRAM-MVVFITANCITINPDIIFA (SEQ ID NO: 27). In some embodiments, the promoter is ActA promoter from WO07/103225; and WO07/117371, each of which is incorporated by reference in its entirety herein.

By way of example, the modified ActA may comprise at least the first 59 amino acids of ActA, or a sequence having at least about 80% sequence identity, at least about 85% sequence identity, at least about 90% sequence identity, at least about 95% sequence identity, or at least about 98% sequence identity to at least the first 59 amino acids of ActA. In some embodiments, the modified ActA comprises at least the first 100 amino acids of ActA, or a sequence having at least about 80% sequence identity, at least about 85% sequence identity, at least about 90% sequence identity, at least about 95% sequence identity, or at least about 98% sequence identity to the first 100 amino acids of ActA. In other words, in some embodiments, the modified ActA sequence corresponds to an N-terminal fragment of ActA (including the ActA signal sequence) that is truncated at residue 100 or thereafter.

ActA-N100 has the following sequence (SEQ ID NO: 28):

```
VGLNRFMRAM MVVFITANCI TINPDIIFAA TDSEDSSLNT    50
DEWEEEKTEE

QPSEVNTGPR YETAREVSSR DIEELEKSNK VKNTNKADLI   100
AMLKAKAEKG
```

In this sequence, the first residue is depicted as a valine; the polypeptide is synthesized by Listeria with a methionine in this position. Thus, ActA-N100 may also have the following sequence (SEQ ID NO:29):

```
MGLNRFMRAM MVVFITANCI TINPDIIFAA TDSEDSSLNT    50
DEWEEEKTEE

QPSEVNTGPR YETAREVSSR DIEELEKSNK VKNTNKADLI   100
AMLKAKAEKG
```

ActA-N100 may also comprise one or more additional residues lying between the C-terminal residue of the modified ActA and the EGFRvIII-derived antigen sequence. In the following sequences, ActA-N100 is extended by two residues added by inclusion of a BamH1 site:

```
                                            (SEQ ID NO: 30)
VGLNRFMRAM MVVFITANCI TINPDIIFAA TDSEDSSLNT    50
DEWEEEKTEE
```

-continued
```
QPSEVNTGPR YETAREVSSR DIEELEKSNK VKNTNKADLI   100
AMLKAKAEKG

GS
``` which when synthesized with a first residue methionine has the sequence:

```
                                            (SEQ ID NO: 31)
MGLNRFMRAM MVVFITANCI TINPDIIFAA TDSEDSSLNT    50
DEWEEEKTEE

QPSEVNTGPR YETAREVSSR DIEELEKSNK VKNTNKADLI   100
AMLKAKAEKG

GS.
```

Thus, an exemplary construct is as follows:
```
                                            (SEQ ID NO: 32)
vglnrfmram mvvfitanci tinpdiifaa tdsedsslnt deweeektee    50 qpsevntgpr yetarevssr dieeleksnk vkntnkadli amlkakaekg   100 gsASKVLPAS RALEEKKGNY VVTDHGSCAD GSVKTSASKV APASRALEEK   150

KGNYVVTDHG SCGDGSIKLS KVLPASRALE EKKGNYVVTD HGSCADGSVK   200

ASKVAPASRA LEEKKGNYVV TDHGSCGDGS IKLSKVLPAS RALEEKKGNY   250

VVTDHGSCAD GSVKTS.
```

In this sequence, the ActA-N100 sequence is in lowercase, the EGFRvIII-derived antigen sequences are underlined, and the linker "cleavable" sequences are not underlined. A corresponding DNA sequence is as follows: gtgggattaaatagatttat- gcgtgcgatgatggtagttttcattactgccaactgcatt acgattaaccccgacat- aatatttgcagcgacagatagcgaagattccagtctaaacaca gatgaatgggaagaagaaaaaacagaa- gagcagccaagcgaggtaaatacgggaccaaga tacgaaactgcacgtgaag- taagttcacgtgatattgaggaactagaaaaatcgaataaa gtgaaaaatacgaa- caaagcagacctaatagcaatgttgaaagcaaaagcagagaaaggt ggatccGCAAGCAAAGTATTGCCAGCTAGTCGTGCAT TAGAGGAGAAAAAGGGGAATTAC GTGGTGACG- GATCATGGATCGTGTGCCGATGGCTCAG- TAAAGACTAGTGCGAGCAAAGTG GCCCCTGCAT- CACGAGCACTTGAAGAGAAAAAGGAAACTATGTT GTGACCGATCATGGT AGCTGCGGAGATGGTTCAAT- TAAATTATCAAAAGTCTTACCAG- CATCTAGAGCTTTAGAG GAAAAGAAGGGTAACTAT- GTCGTAACAGATCATGGAAGTTGTGCTGACGGAAG TGTTAAA GCGTCGAAAGTAGCTCCAGCTTCTCGCG- CATTAGAAGAAAAAGAAAGGCAATTATGTTGTA ACA- GACCATGGTAGTTGTGGTGATGGCTC- GATCAAATTGTCAAAAGTTCTACCGGCTTCT CGTGCGCTAGAAGAGAAGAAAGGAAAT- TACGTAGTTACAGACCACGGCTCTTGCGCGGAT GGTTCCGTTAAAACTAGT (SEQ ID NO: 33). In this sequence, the ActA-N100 sequence is in lowercase, a BamHI cloning site is underlined, and the EGFRvIII-derived antigen and linker "cleavable" sequences are not underlined. This sequence may be preceded by an ActA promoter sequence, such as

```
                                            (SEQ ID NO: 34)
gggaagcagttggggttaactgattaacaaatgttagagaaaaattaattctccaagtga tattcttaaaataattcatgaatatttttcttatattagctaattaagaagataattaa ctgctaatccaatttttaacggaataaattagtgaaaatgaaggccgaattttccttgtt ctaaaaaggttgtattagcgtatcacgaggagggagtataa.
```

Exemplary constructs are described hereinafter and in WO07/103225, which is incorporated by reference herein. ANZ-100 (formerly known as CRS-100; BB-IND 12884 and clinicaltrials.gov identifier NCT00327652) consists of a *L. monocytogenes* ΔactA/ΔinlB platform without any exogenous antigen expression sequences. In the exemplary constructs described in WO07/103225, this platform has been engineered to express human Mesothelin as a fusion with ActA-N100. The mesothelin expression vaccine has been evaluated in subjects with advanced carcinoma with liver metastases using CRS-207 (BB-IND 13389 and clinicaltrials.gov identifier NCT00585845). The present invention contemplates modification of this vaccine by replacing the mesothelin sequences with EGFRvIII-derived antigen sequences.

As sequences encoded by one organism are not necessarily codon optimized for optimal expression in a chosen vaccine platform bacterial strain, the present invention also provides nucleic acids that are altered by codon optimized for expressing by a bacterium such as *L. monocytogenes*.

In various embodiments, at least one percent of any non-optimal codons are changed to provide optimal codons, more normally at least five percent are changed, most normally at least ten percent are changed, often at least 20% are changed, more often at least 30% are changed, most often at least 40%, usually at least 50% are changed, more usually at least 60% are changed, most usually at least 70% are changed, optimally at least 80% are changed, more optimally at least 90% are changed, most optimally at least 95% are changed, and conventionally 100% of any non-optimal codons are codon-optimized for *Listeria* expression (Table 2).

TABLE 2

Optimal codons for expression in *Listeria*.

| | Amino Acid | | | | | | | | |
|---|---|---|---|---|---|---|---|---|---|
| | A | R | N | D | C |

TABLE 3-continued

Strains of *Listeria* suitable for use in the present invention, e.g., as a vaccine or as a source of nucleic acids.

| | |
|---|---|
| *L. monocytogenes* DP-L4029 deleted in uvrAB. | U.S. Provisional Pat. Appl. Ser. No. 60/541,515 filed Feb. 2, 2004; U.S. Provisional Pat. Appl. Ser. No. 60/490,080 filed Jul. 24, 2003. |
| *L. monocytogenes* DP-L4029 deleted in uvrAB treated with a psoralen. | U.S. Provisional Pat. Appl. Ser. No. 60/541,515 filed Feb. 2, 2004. |
| *L. monocytogenes* delta actA delta inlB delta uvrAB | Brockstedt (2005) Nature Medicine and KBMA patent |
| *L. monocytogenes* delta actA delta inlB delta uvrAB treated with psoralen | Brockstedt (2005) Nature Medicine and KBMA patent |
| *L. monocytogenes* delta actA delta inlB delta uvrAB prfA(G155S) | Lauer et al, (2008) Infect. Immun. And WO 2009/143085 |
| *L. monocytogenes* delta actA delta inlB delta uvrAB prfA(G155S) treated with psoralen | Lauer et al, (2008) Infect. Immun. And WO 2009/143085 |
| *L. monocytogenes* ActA-/inlB-double mutant. | Deposited with ATCC on Oct. 3, 2003. Acc. No. PTA-5562. |
| *L. monocytogenes* lplA mutant or hly mutant. | U.S. Pat. Applic. No. 20040013690 of Portnoy, et al. |
| *L. monocytogenes* DAL/DAT double mutant. | U.S. Pat. Applic. No. 20050048081 of Frankel and Portnoy. |
| *L. monocytogenes* str. 4b F2365. | GenBank Acc. No. NC_002973. |
| *Listeria ivanovii* | ATCC No. 49954 |
| *Listeria innocua* Clip11262. | GenBank Acc. No. NC_003212; AL592022. |
| *Listeria innocua*, a naturally occurring hemolytic strain containing the PrfA-regulated virulence gene cluster. | Johnson, et al. (2004) Appl. Environ. Microbiol. 70: 4256-4266. |
| *Listeria seeligeri*. | Howard, et al. (1992) Appl. Eviron. Microbiol. 58: 709-712. |
| *Listeria innocua* with *L. monocytogenes* pathogenicity island genes. | Johnson, et al. (2004) Appl. Environ. Microbiol. 70: 4256-4266. |
| *Listeria innocua* with *L. monocytogenes* internalin A gene, e.g., as a plasmid or as a genomic nucleic acid. | See, e.g., Lingnau, et al. (1995) Infection Immunity 63: 3896-3903; Gaillard, et al. (1991) Cell 65: 1127-1141). |

The present invention encompasses reagents and methods that comprise the above Listerial strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); daaA (dat; D-amino acid aminotransferase); plcA; plcB; ActA; or any nucleic acid that mediates growth, spread, breakdown of a single walled vesicle, breakdown of a double walled vesicle, binding to a host cell, uptake by a host cell. The present invention is not to be limited by the particular strains disclosed above.

Targeting antigens to endocytic receptors on professional antigen-presenting cells (APCs) also represents an attractive strategy to enhance the efficacy of vaccines. Such APC-targeted vaccines have an exceptional ability to guide exogenous protein antigens into vesicles that efficiently process the antigen for major histocompatibility complex class I and class II presentation. Efficient targeting not only requires high specificity for the receptor that is abundantly expressed on the surface of APCs, but also the ability to be rapidly internalised and loaded into compartments that contain elements of the antigen-processing machinery. In these embodiments, the antigens of the present invention are provided as fusion constructs which include an immunogenic EGFRvIII-derived antigen polypeptide and a desired endocytic receptor-targeting moiety. Suitable APC endocytic receptors include DEC-205, mannose receptor, CLEC9, Fc receptor. This list is not meant to be limiting. A receptor-targeting moiety may be coupled to an immunogenic EGFRvIII-derived antigen polypeptide by recombinant or using chemical crosslinking.

4. Therapeutic Compositions.

The vaccine compositions described herein can be administered to a host, either alone or in combination with a pharmaceutically acceptable excipient, in an amount sufficient to induce an appropriate immune response. The immune response can comprise, without limitation, specific immune response, non specific immune response, both specific and non specific response, innate response, primary immune response, adaptive immunity, secondary immune response, memory immune response, immune cell activation, immune cell proliferation, immune cell differentiation, and cytokine expression. The vaccines of the present invention can be stored, e.g., frozen, lyophilized, as a suspension, as a cell paste, or complexed with a solid matrix or gel matrix.

In certain embodiments, after the subject has been administered an effective dose of a vaccine containing the immunogenic EGFRvIII-derived antigen polypeptides to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost."

As an example, a first vaccine comprised of killed but metabolically active *Listeria* that encodes and expresses the antigen polypeptide(s) may be delivered as the "prime," and a second vaccine comprised of attenuated (live or killed but metabolically active) *Listeria* that encodes the antigen polypeptide(s) may be delivered as the "boost." It should be understood, however, that each of the prime and boost need not utilize the methods and compositions of the present invention. Rather, the present invention contemplates the use of other vaccine modalities together with the bacterial vaccine methods and compositions of the present invention. The following are examples of suitable mixed prime-boost regimens: a DNA (e.g., plasmid) vaccine prime/bacterial vaccine boost; a viral vaccine prime/bacterial vaccine boost; a protein vaccine prime/bacterial vaccine boost; a DNA prime/bacterial vaccine boost plus protein vaccine boost; a bacterial vaccine prime/DNA vaccine boost; a bacterial vaccine prime/viral vaccine boost; a bacterial vaccine prime/protein vaccine boost; a bacterial vaccine prime/bacterial vaccine boost plus protein vaccine boost; etc. This list is not meant to be limiting The prime vaccine and boost vaccine may be administered by the same route or by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine or vaccines in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

In certain embodiments, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days, about 6 months, and about 1 year after administration of the prime vaccination is initiated. Preferably one or both of the prime and boost vaccination comprises delivery of a composition of the present invention.

A "pharmaceutically acceptable excipient" or "diagnostically acceptable excipient" includes but is not limited to, sterile distilled water, saline, phosphate buffered solutions, amino acid based buffers, or bicarbonate buffered solutions. An excipient selected and the amount of excipient used will depend upon the mode of administration. Administration may be oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration. The administration can comprise an injection, infusion, or a combination thereof.

Administration of the vaccine of the present invention by a non oral route can avoid tolerance. Methods are known in the art for administration intravenously, subcutaneously, intramuscularly, intraperitoneally, orally, mucosally, by way of the urinary tract, by way of a genital tract, by way of the gastrointestinal tract, or by inhalation.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The vaccines of the present invention can be administered in a dose, or dosages, where each dose comprises at least 100 bacterial cells/kg body weight or more; in certain embodiments 1000 bacterial cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight. The present invention provides the above doses where the units of bacterial administration is colony forming units (CFU), the equivalent of CFU prior to psoralen treatment, or where the units are number of bacterial cells.

The vaccines of the present invention can be administered in a dose, or dosages, where each dose comprises between $10^7$ and $10^8$ bacteria per 70 kg body weight (or per 1.7 square meters surface area; or per 1.5 kg liver weight); $2\times10^7$ and $2\times10^8$ bacteria per 70 kg body weight (or per 1.7 square meters surface area; or per 1.5 kg liver weight); $5\times10^7$ and $5\times10^8$ bacteria per 70 kg body weight (or per 1.7 square meters surface area; or per 1.5 kg liver weight); $10^8$ and $10^9$ bacteria per 70 kg body weight (or per 1.7 square meters surface area; or per 1.5 kg liver weight); between $2.0\times10^8$ and $2.0\times10^9$ bacteria per 70 kg (or per 1.7 square meters surface area, or per 1.5 kg liver weight); between $5.0\times10^8$ to $5.0\times10^9$ bacteria per 70 kg (or per 1.7 square meters surface area, or per 1.5 kg liver weight); between $10^9$ and $10^{10}$ bacteria per 70 kg (or per 1.7 square meters surface area, or per 1.5 kg liver weight); between $2\times10^9$ and $2\times10^{10}$ bacteria per 70 kg (or per 1.7 square meters surface area, or per 1.5 kg liver weight); between $5\times10^9$ and $5\times10^{10}$ bacteria per 70 kg (or per 1.7 square meters surface area, or per 1.5 kg liver weight); between $10^{11}$ and $10^{12}$ bacteria per 70 kg (or per 1.7 square meters surface area, or per 1.5 kg liver weight); between $2\times10^{11}$ and $2\times10^{12}$ bacteria per 70 kg (or per 1.7 square meters surface area, or per 1.5 kg liver weight); between $5\times10^{11}$ and $5\times10^{12}$ bacteria per 70 kg (or per 1.7 square meters surface area, or per 1.5 kg liver weight); between $10^{12}$ and $10^{13}$ bacteria per 70 kg (or per 1.7 square meters surface area); between $2\times10^{12}$ and $2\times10^{13}$ bacteria per 70 kg (or per 1.7 square meters surface area, or per 1.5 kg liver weight); between $5\times10^{12}$ and $5\times10^{13}$ bacteria per 70 kg (or per 1.7 square meters surface area, or per 1.5 kg liver weight); between $10^{13}$ and $10^{14}$ bacteria per 70 kg (or per 1.7 square meters surface area, or per 1.5 kg liver weight); between $2\times10^{13}$ and $2\times10^{14}$ bacteria per 70 kg (or per 1.7 square meters surface area, or per 1.5 kg liver weight); $5\times10^{13}$ and $5\times10^{14}$ bacteria per 70 kg (or per 1.7 square meters surface area, or per 1.5 kg liver weight); between $10^{14}$ and $10^{15}$ bacteria per 70 kg (or per 1.7 square meters surface area, or per 1.5 kg liver weight); between $2\times10^{14}$ and $2\times10^{15}$ bacteria per 70 kg (or per 1.7 square meters surface area, or per 1.5 kg liver weight); and so on, wet weight.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial bacterial dose, followed by relatively small subsequent doses, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering *Listeria* that is oral. Also provided is a method of administering *Listeria* that is intravenous. Moreover, what is provided is a method of administering *Listeria* that is oral, intramuscular, intravenous, intradermal and/or subcutaneous. The invention supplies a *Listeria* bacterium, or culture or suspension of *Listeria* bacteria, prepared by growing in a medium that is meat based, or that contains polypeptides derived from a meat or animal product. Also supplied by the present invention is a *Listeria* bacterium, or culture or suspension of *Listeria* bacteria, prepared by growing in a medium that does not contain meat or animal products, prepared by growing on a medium that contains vegetable polypeptides, prepared by growing on a medium that is not based on yeast products, or prepared by growing on a medium that contains yeast polypeptides.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Additional agents which are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types aas macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleoteide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and other like immune modulators used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The reagents and methods of the present invention provide a vaccine comprising only one vaccination; or comprising a first vaccination; or comprising at least one booster vaccination; at least two booster vaccinations; or at least three booster vaccinations. Guidance in parameters for booster vaccinations is available. See, e.g., Marth (1997) Biologicals 25:199-203; Ramsay, et al. (1997) Immunol. Cell Biol. 75:382-388; Gherardi, et al. (2001) Histol. Histopathol. 16:655-667; Leroux-Roels, et al. (2001) ActA Clin. Belg. 56:209-219; Greiner, et al. (2002) Cancer Res. 62:6944-6951; Smith, et al. (2003) J. Med. Virol. 70:Suppl.1:S38-S41; Sepulveda-Amor, et al. (2002) Vaccine 20:2790-2795).

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

EXAMPLES

The following examples serve to illustrate the present invention. These examples are in no way intended to limit the scope of the invention.

Example 1

Bacterial Strains and Antigen Selection

Lm vaccine strains were constructed in two strain backgrounds, live-attenuated (Lm11, aka Lm ΔactA/ΔinlB) and KBMA PrfA* (Lm677, aka Lm ΔactA/ΔinlB/ΔuvrAB/prfA G155S). Expression cassettes were designed to contain 1 and 5 copies of the sequence PASRALEEKKGNYVVTDHGSC (SEQ ID NO: 4) (denoted PvIII in FIG. 1), each copy flanked by a proteasome cleavage sequence (black boxes in FIG. 1). The expression cassettes were codon optimized for expression in *L. monocytogenes* and cloned as BamHI-SpeI fragments downstream from the actA promoter and in-frame with the 100 amino terminal acids of ActA ("ActA-N100") and tagged at the carboxy terminus with SIINFEKL (SL8), a surrogate T-cell epitope that facilitates evaluation of expression and secretion of encoded heterologous antigens. The constructs were cloned into a derivative of the pPL2 integration vector and stably integrated at the $tRNA^{Arg}$ locus of the bacterial chromosome.

The tested strains are summarized in the following table:

| Strain | Construct | Background |
| --- | --- | --- |
| BH137 | ActAN100-AH1A5-OVA | Lm11 (ΔactAΔinlB) |
| Lm11 | Negative control | |
| PL712 | ActAN100-PepVIIIx5-SL8 | Lm11 |
| PL714 | ActAN100-PepVIIIx5-SL8 | Lm677 (prfA*) |
| PL716 | ActAN100-PepVIIIx1-SL8 | Lm11 |
| PL717 | ActAN100-PepVIIIx1-SL8 | Lm677 (prfA*) |

Example 2

In vitro Cell Culture

J774 cells were cultured in T cell media (RPMI media (Invitrogen, Carlsbad, Calif.) supplemented with 10% FBS (Hyclone, Logan, Utah), penicillin/streptomycin (Mediatech, Manassas, Va.), 1× non-essential amino acids (Mediatech, Manassas, Va.), 2 mM L-glutamine (Mediatech, Manassas, Va.), HEPES buffer (Invitrogen, Carlsbad, Calif.), 1 mM sodium pyruvate (Sigma, St. Louis, Mo.), and 50 µM β-mercaptoethanol (Sigma, St. Louis, Mo.)). B3Z hybridoma cells were cultured in T cell media without penicillin/streptomycin.

Example 4

Figure 3:
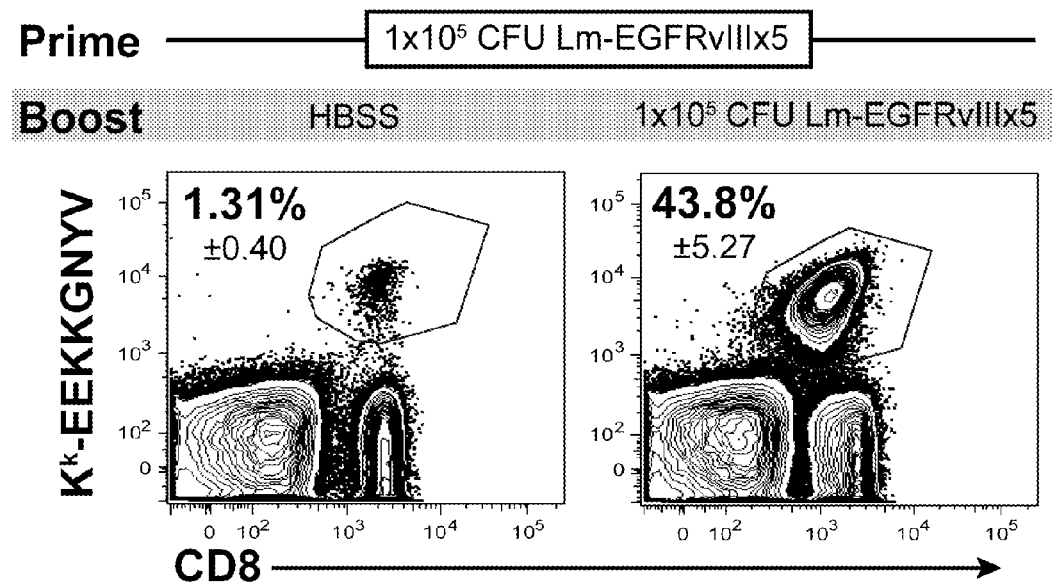
FIG. 3 depicts EGFRvIII antigen-specific CD8+ T cells induced by immunization with recombinant *Listeria*.

Immunizations 6-12 week old female C3H/HeJ mice were obtained from Charles River Laboratories (Wilmington, Mass.). Studies were performed under animal protocols approved by the appropriate Institutional Animal Care and Use Committee. Live-attenuated bacteria were prepared for immunization from overnight cultures grown in yeast extract media. Bacteria were diluted in Hank's balanced salt solution (HBSS) for injection. Live-attentuated bacteria were administered i.v. into tail vein in 200 µL volume. Injection stocks of live-attenuated bacteria were plated to confirm colony forming units (CFU) Animals were primed and boosted female with 1×10⁷ CFU Lm ΔactAΔinlBprfA*-5× EGFRvIII$_{20-40}$ separated by 30 days, and the frequency of EGFRvIII-specific CD8+ T cells determined by intracellular cytokine staining (FIG. 3).

Example 5

Assessment of Antigen Expression and Immune Response a. Western Blots

Figure 2:
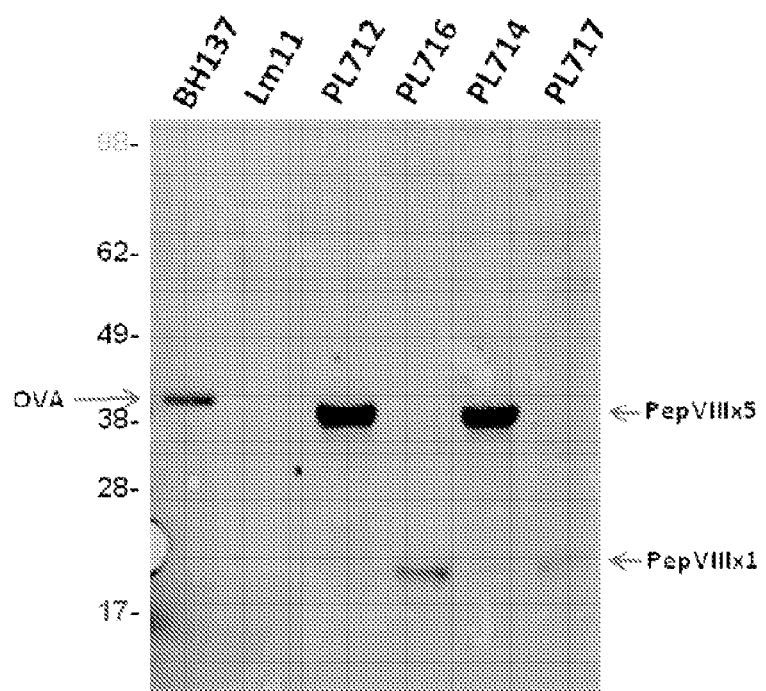
FIG. 2 depicts Western blot results demonstrating expression of EGFRvIII antigens by recombinant *Listeria*.

Western blots from broth culture were performed on equivalent amounts of TCA-precipitated supernatants of bacterial cultures grown in yeast extract media to an $OD_{600}$ of 0.7 (late log). For western blots from Lm infected DC2.4 cells were inoculated with a multiplicity of infection (MOI) of 10 for 1 hour, the cells were washed 3× with PBS and DMEM media supplemented with 50 µg/mL gentamycin. Cells were harvested at 7 hours post infection. Cells were lysed with SDS sample buffer, collected and run on 4-12% polyacrylamide gels and transferred to nitrocellulose membranes for western blot analysis. All western blots utilized a polyclonal antibody raised against the mature N-terminus of the ActA protein and were normalized to p60 expression (an unrelated Lm protein) with an anti-p60 monoclonal antibody. Antigen detection was visualized either by enhanced chemiluminescence (ECL) or visualized and quantitated with the Licor Odyssey IR detection system (FIG. 2)

b. B3Z Assay

Figure 4:
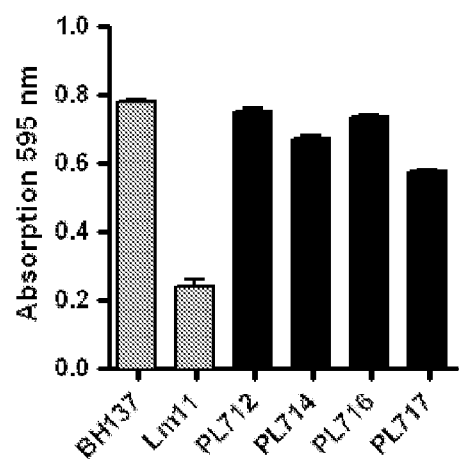
FIG. 4 depicts the results obtained from a B3Z T cell activation assay following immunization with recombinant *Listeria*.

DC2.4 cells were infected with the selected strains, and incubated with the $OVA_{257-264}$-specific T cell hybridoma, B3Z. Presentation of SIINFEKL epitope on H-2 $K^b$ class I molecules was assessed by measuring β-galactosidase expression using a chromogenic substrate (FIG. 4).

c. Reagents for Flow Cytometry

CD4 FITC (clone GK1.5) and MHC class II FITC (clone M5/114.15.2) were purchased from eBioscience (San Diego, Calif.). CD8a antibody PerCP (clone 53-6.7) was purchased from BD Biosciences (San Jose, Calif.). The Kk-EEKKGNYV (SEQ ID NO: 3) tetramer was folded by the NIH Tetramer Core and conjugated to APC.

d. Tetramer Staining of EGFRvIII-Specific T Cells

Splenocytes (lymphocytes from the spleen) were incubated with anti-CD4, anti-CD8, anti-MHC class II and Kk-EGFRvIII tetramer for 15 minutes at room temperature. Cells were washed three times with HBSS. Samples were acquired using a LSRII flow cytometer (BD Biosciences). Data were gated to include exclusively CD8+, CD4-class II-events, then the percentage of these cells binding Kk-EEKKGNYV (SEQ ID NO: 3) tetramer was determined Data was analyzed using FlowJo software (Treestar, Ashland, Oreg.).

Example 6

Results

As can be seen from FIG. 2, all of the EGFRvIII$_{20-40}$ constructs were detected within J774 macrophages. Furthermore, we found that increasing the copies of EGFRvIII$_{20-40}$ appears to enhance intracellular secretion (FIG. 2). The amount of 5× EGFRvIII$_{20-40}$ secreted exceeded that of the "gold-standard" ovalbumin. In animals, receiving the 5× EGFRvIII$_{20-40}$ construct, greater than 30% of the CD8+ T cells in the spleen were EGFRvIII-specific 5 days following boost immunization (FIG. 3). All of the EGFRvIII$_{20-40}$ constructs tested are recognized by the B3Z T cell, indicating successful expression and presentation of T cell epitopes by the *L. monocytogenes* strains at a level roughly equivalent to the model ovalbumin antigen (FIG. 4).

These data suggest that an EGFRvIII$_{20-40}$ expression construct, and particularly a multimeric EGFRvIII$_{20-40}$ expression construct, is well suited for use within this *L. monocytogenes* vaccine platform.

Example 7

Evaluating an Immune Response with EEKKGNYV (SEQ ID NO: 3)

Precise identification of class I restricted epitopes provides an optimized method for assessing immunogenicity in vivo, simplifying comparisons of our vaccine candidates. To identify mouse class I-restricted epitopes, as well as to perform a cursory evaluation of immunogenicity, C57BL/6 (H-2$^b$), BALB/c (H-2$^d$), C3H/HeJ (H-2$^k$) and SJL (H-2$^s$) mice were immunized with 1×10$^7$ colony forming units (CFU) of each EGFRvIII$_{20-40}$ expressing strain and the frequency and specificity of EGFRvIII-specific T cells was determined by IFN-γ intracellular cytokine staining (ICS). This library uses 15-AA peptides overlapping by 14-AA, possible due to the short sequence of the EGFRvIII$_{20-40}$ peptide in our vaccine, and desirable due to the known N-terminal processing issues associated with these libraries. The greatest response was in the C3H mouse strain (H-2$^k$), where >1% of total CD8+ T cells in the spleen responded to one of the 15-AA peptides (data not shown).

Figure 5:
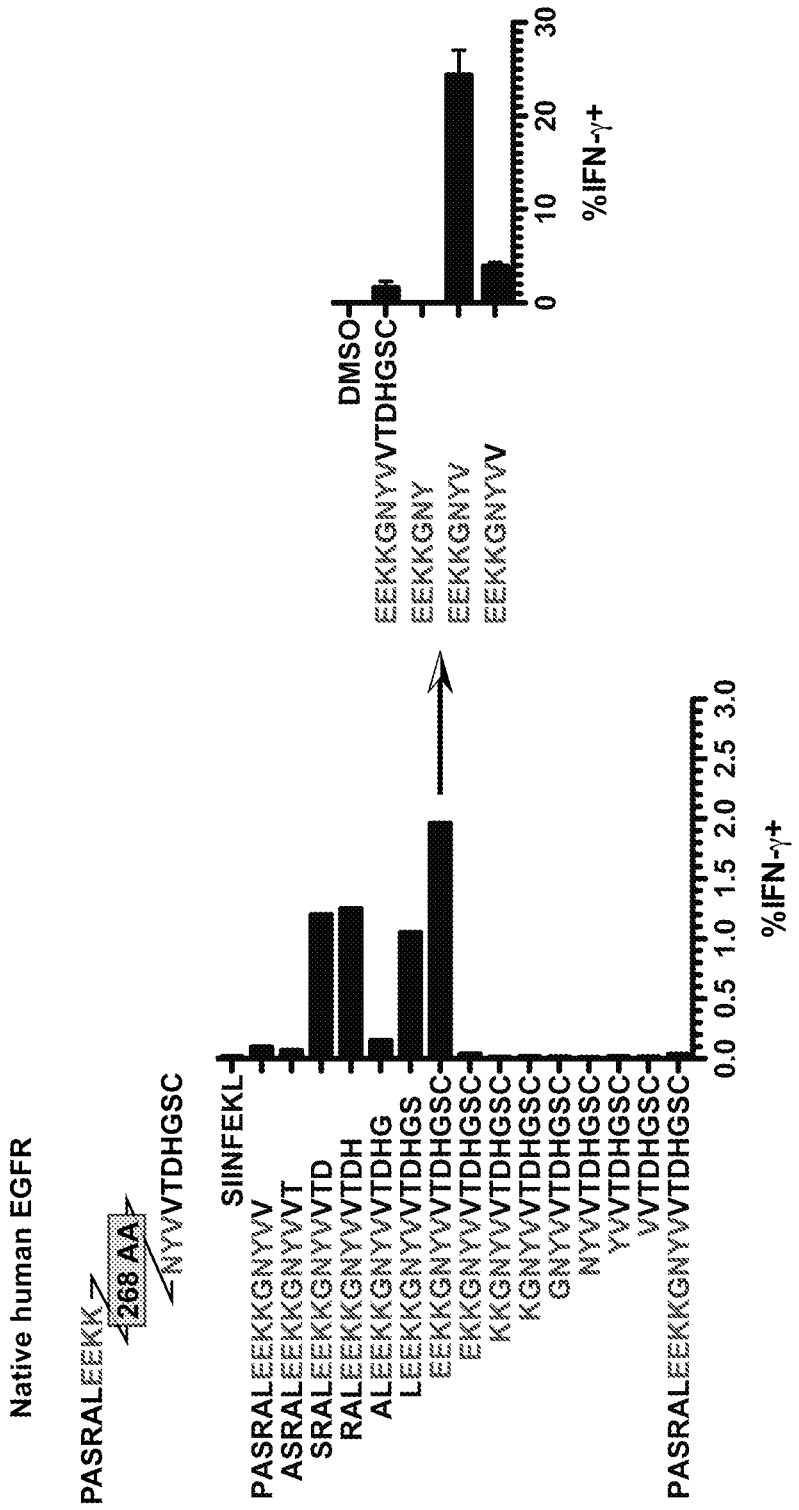
FIG. 5 depicts the results obtained from screening of CD8+ T cells for reactivity against specific EGFRvIII peptides following immunization with recombinant *Listeria*.

To confirm this finding and refine the exact sequence of the class I-binding peptide, a cohort of C3H mice were primed and boosted with the Lm-EGFRvIIIx5 strain, and then screened again with the peptide library. In addition, we included refined peptides from the 15-mer identified in the primary immunogenicity assay. CD8+ T cells from these primed and boosted mice recognized several of the 15-AA peptides, and reactivity was dependent upon two N-terminal glutamic acid residues. Assuming these two glutamic acid residues were necessary for MHC binding, we used 7-, 8- and 9-mers from this sequence and screened for reactivity (FIG. 5).

Figure 6:
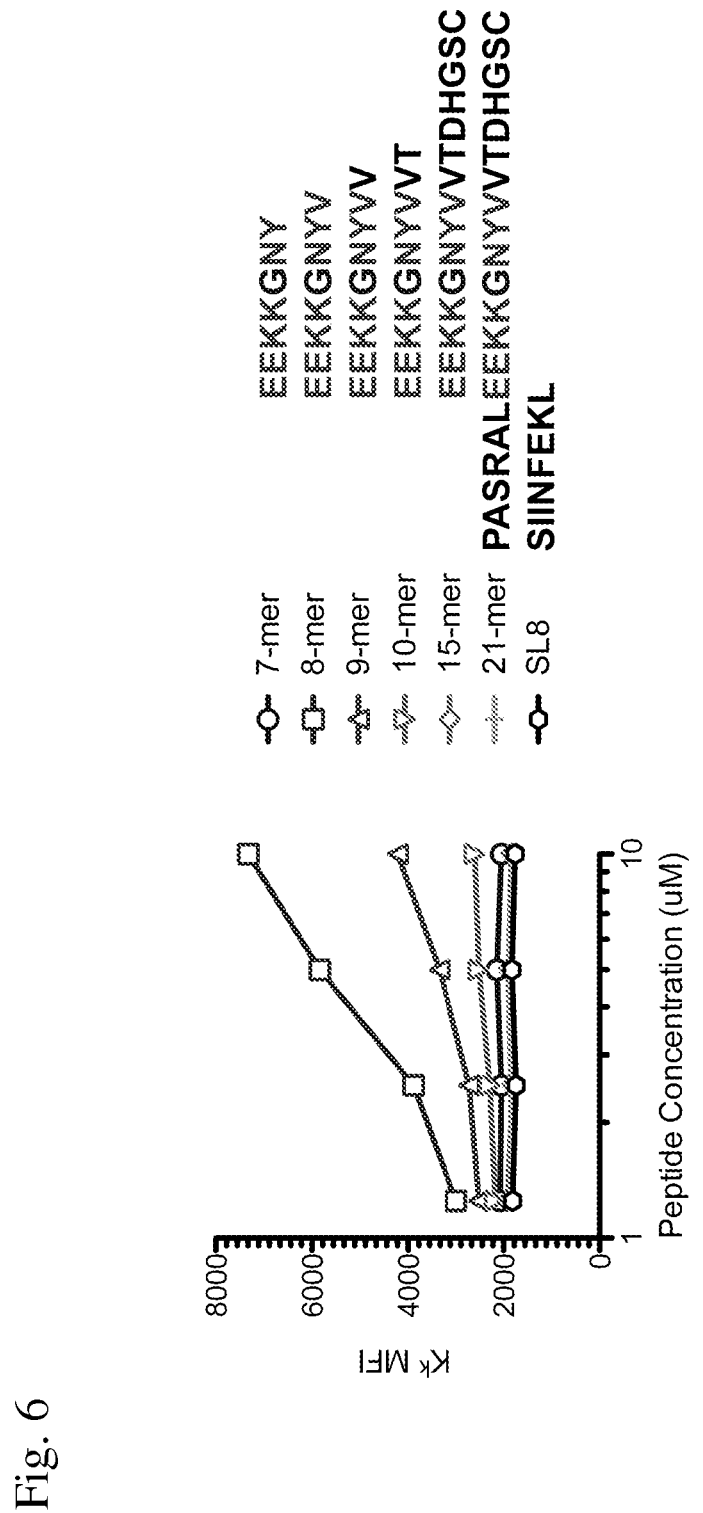
FIG. 6 depicts the results obtained from a T2 cell assay measuring induction of class I expression upon EGFRvIII peptide binding.

Identification of a class I-restricted EGFRvIII-epitope in C3H mice. Female C3H mice were primed and boosted with Lm-EGFRvIIIx5, and then five days later spleens were harvested and tested for reactivity with the EGFRvIII peptide library, as well as 7-, 8-, and 9-mers derived from the peptide with the greatest reactivity in a preliminary screen. Data represent the % IFN-γ+ events within the CD8+ T cell gate. These experiments demonstrated that the 8-AA peptide EEKKGNYV (SEQ ID NO: 3) is recognized by CD8+ T cells from C3H mice immunized TAP-deficient T2 cells are unable to load class I molecules with peptides, leading to instability and recycling from the cell surface. When exogenous peptides are added that can bind the expressed MHC molecule, that molecule is stabilized on the cell surface with Lm-EGFRvIII. To confirm k$^k$ binding of the EEKKGNYV (SEQ ID NO: 3) peptide, A T2 cell assay which measures such induction of class I expression upon peptide binding was used substantially as described by Hansen and Myers (2003) Peptide induction of surface expression of class I MHC, p. 18.11.1-18.11.8 in J. E. Colgan, A. M. Kruisbeer, D. H. Marguiles, and W. Strober (ed.), Current Protocols in Immunology, vol. 4. John Wiley & Sons, New York, N.Y. K$^k$-expressing T2 cells were incubated overnight with the concentration of each EGFRvIII peptide as indicated in FIG. 6. Cells were washed and stained for surface K$^k$ expression using a class I-specific antibody. The data demonstrate that EEKKGNYV binds K$^k$ and is optimal relative to the larger peptides that also contain this sequence. These data support the use of the defined EEKKGNYV peptide for ex vivo cellular assays based on its ability to bind K$^k$ and provide MHC-peptide complexes that can be recognized by CD8+ T cells.

Using this defined class I restricted peptide, we compared the magnitude of the primary EGFRvIII-specific CD8+ T cell response after immunization with each strain. Female C3H mice were immunized with 1×10$^5$ CFU of the 1× or 5× strains, and seven days later spleens were harvested and the frequency of EGFRvIII$_{26-33}$-specific CD8+ T cells determined by ICS. Consistent with our hypothesis, the inclusion of multiple copies of EGFRvIII$_{20-40}$ led to enhanced CD8+ T cell priming relative to the single copy variant (FIG. 7).

These data demonstrate the ability to express a construct encoding repeating epitope sequences, but altering codon usage to maximize genetic stability and antigen expression/secretion. This approach allows for increased potency without increasing potential risks to the patient (i.e. by giving large doses of vaccine).

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A composition comprising:

a bacterium or virus which comprises a nucleic acid encoding at least one immunogenic polypeptide, the amino acid sequence of which comprise a plurality of EGFRvIII polypeptide sequences, the sequence of which each comprise EEKKGNYV (SEQ ID NO: 3), and wherein said plurality of EGFRvIII polypeptide sequences comprise at least three copies of PASRALEEKKGNYVVTDHGSC (SEQ ID NO: 5).

2. The composition of claim 1 wherein said plurality of EGFRvIII polypeptide sequences comprise at least five copies of PASRALEEKKGNYVVTDHGSC (SEQ ID NO: 5).

3. The composition of claim 1, wherein each EGFRvIII polypeptide sequence is flanked by a sequence which is configured to be cleaved by the proteasome.

4. A pharmaceutical composition comprising:

the composition of claim 1; and a pharmaceutically acceptable excipient.

5. The composition of claim 1 wherein composition comprises an attenuated *Listeria monocytogenes* bacterium comprising said nucleic acid.

6. The composition of claim 5, wherein the composition comprises a *Listeria monocytogenes* bacterium comprising said nucleic acid integrated into the genome of said bacterium.

7. The composition of claim 5, wherein the bacterium is an actA deletion mutant or an actA insertion mutant, an inlB deletion mutant or an inlB insertion mutant or a ΔactA/ΔinlB mutant comprising both an actA deletion or an actA insertion and an inlB deletion or an inlB insertion.

8. The composition of claim 5, wherein said nucleic acid has been integrated into a virulence gene of said bacterium, and the integration of the polynucleotide disrupts expression of the virulence gene or disrupts a coding sequence of the virulence gene.

9. The composition of claim 8, wherein the virulence gene is actA or inlB.

10. The composition of claim 9, wherein the bacterium is Lm ΔactA/ΔinlB.

11. The composition of claim 7, wherein the bacterium further comprises a genetic mutation that attenuates the ability of the bacterium to repair nucleic acid.

12. The composition of claim 11, wherein the genetic mutation is in one or more genes selected from phrB, uvrA, uvrB, uvrC, uvrD and recA.

13. The composition of claim 9, wherein the bacterium is a *Listeria monocytogenes* prfA mutant, the genome of which encodes a prfA protein which is constitutively active.

14. The composition of claim 10, wherein the bacterium is a killed but metabolically active *Listeria monocytogenes*.

15. The composition of claim 5, wherein the bacterium is a *Listeria monocytogenes* prfA mutant, the genome of which encodes a prfA protein which is constitutively active.

16. The composition of claim 5, wherein the nucleic acid is codon optimized for expression by *Listeria monocytogenes*.

17. The composition of claim 5, wherein said composition further comprises a pharmaceutically acceptable excipient.

18. The composition of any one of claims 5, wherein said nucleic acid encodes said immunogenic polypeptide as a fusion protein comprising a secretory signal sequence.

19. The composition of claim 18, wherein the secretory signal sequence is a *Listeria monocytogenes* ActA signal sequence.

20. The composition of claim 19, wherein said nucleic acid molecule encodes said immunogenic polypeptide as a fusion protein comprising an in frame ActA-N100 sequence selected from the group consisting of selected from the group consisting of SEQ ID NO: 28, SEQ ID NO: 29, SEQ ID NO: 30, and SEQ ID NO: 31, or an amino acid sequence having at least 90% sequence identity to said ActA-N100 sequence.

21. The composition of claim 5, wherein said nucleic acid encodes said immunogenic polypeptide as a fusion protein, wherein:
    each of the plurality of EGFRvIII polypeptide sequences has the sequence PASRALEEKKGNYVVTDHGSC (SEQ ID NO: 5);
    each of the plurality of EGFRvIII polypeptide sequences is flanked by a sequence which is configured to be cleaved by the proteasome;
    said fusion protein further comprises an ActA-N100 sequence selected from the group consisting of SEQ ID NO: 28, SEQ ID NO: 29, SEQ ID NO: 30, and SEQ ID NO: 31 or an amino acid sequence having at least 90% sequence identity to said ActA-N100 sequence; and
    said fusion protein is expressed from a nucleic acid sequence operably linked to a *Listeria monocytogenes* ActA promoter.

* * * * *

SEQUENCE LISTING

<160> NUMBER OF SEQ ID NOS: 59

<210> SEQ ID NO 1
<211> LENGTH: 10
<212> TYPE: PRT
<213> ORGANISM: Homo sapiens

<400> SEQUENCE: 1

Leu Glu Glu Lys Lys Gly Asn Tyr Val Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Glu Glu Lys Lys Gly Asn Tyr Val Val Thr Asp His
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Glu Lys Lys Gly Asn Tyr Val
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Glu Glu Lys Lys Gly Asn Tyr Val
1               5

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Ala Ser Arg Ala Leu Glu Glu Lys Lys Gly Asn Tyr Val Val Thr
1               5                   10                  15

Asp His Gly Ser Cys
            20

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic

```
<400> SEQUENCE: 6

Ala Ser Lys Val Leu Ala Asp Gly Ser Val Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ser Lys Val Ala Gly Asp Gly Ser Ile Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ser Lys Val Leu Ala Asp Gly Ser Val Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Ala Lys Ser Leu Ala Asp Leu Ala Val Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ser Val Val Ala Gly Ile Gly Ser Ile Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Val Glu Lys Ile Asn Ala Ala Asn Lys Gly
1               5                   10

<210> SEQ ID NO 12
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Gly Ser Lys Lys Ala Gly Asp Gly Asn Lys Lys
1               5                   10

<210> SEQ ID NO 13
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser Lys Val Leu Ala Asp Gly Ser Val Lys Ala Ser Lys Val Ala
1               5                   10                  15

Gly Asp Gly Ser Ile Lys Leu Ser Lys Val Leu Ala Asp Gly Ser Val
            20                  25                  30

Lys Ala Ser Lys Val Ala Gly Asp Gly Ser Ile Lys Leu Ser Lys Val
        35                  40                  45

Leu Ala Asp Gly Ser Val Lys
    50                  55

<210> SEQ ID NO 14
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Ser Lys Val Leu Ala Asp Gly Ser Val Lys Asp Gly Ser Lys Lys
1               5                   10                  15

Ala Gly Asp Gly Asn Lys Lys Leu Ser Lys Val Leu Ala Asp Gly Ser
            20                  25                  30

Val Lys Asp Gly Ser Lys Lys Ala Gly Asp Gly Asn Lys Lys Leu Ser
        35                  40                  45

Lys Val Leu Ala Asp Gly Ser Val Lys Asp Gly Ser Lys Lys Ala Gly
    50                  55                  60

Asp Gly Asn Lys Lys
65

<210> SEQ ID NO 15
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ser Lys Val Leu Pro Ala Ser Arg Ala Leu Glu Glu Lys Lys Gly
1               5                   10                  15

Asn Tyr Val Val Thr Asp His Gly Ser Cys Ala Asp Gly Ser Val Lys
            20                  25                  30

Thr Ser Ala Ser Lys Val Ala Pro Ala Ser Arg Ala Leu Glu Glu Lys
```

```
                35                  40                  45
Lys Gly Asn Tyr Val Val Thr Asp His Gly Ser Cys Gly Asp Gly Ser
 50                  55                  60
Ile Lys Leu Ser Lys Val Leu Pro Ala Ser Arg Ala Leu Glu Glu Lys
 65                  70                  75                  80
Lys Gly Asn Tyr Val Val Thr Asp His Gly Ser Cys Ala Asp Gly Ser
                 85                  90                  95
Val Lys Ala Ser Lys Val Ala Pro Ala Ser Arg Ala Leu Glu Glu Lys
                100                 105                 110
Lys Gly Asn Tyr Val Val Thr Asp His Gly Ser Cys Gly Asp Gly Ser
                115                 120                 125
Ile Lys Leu Ser Lys Val Leu Pro Ala Ser Arg Ala Leu Glu Glu Lys
                130                 135                 140
Lys Gly Asn Tyr Val Val Thr Asp His Gly Ser Cys Ala Asp Gly Ser
145                 150                 155                 160
Val Lys Thr Ser

<210> SEQ ID NO 16
<211> LENGTH: 237
<212> TYPE: PRT
<213> ORGANISM: Listeria monocytogenes

<400> SEQUENCE: 16

Met Asn Ala Gln Ala Glu Glu Phe Lys Lys Tyr Leu Glu Thr Asn Gly
 1               5                  10                  15
Ile Lys Pro Lys Gln Phe His Lys Lys Glu Leu Ile Phe Asn Gln Trp
                20                  25                  30
Asp Pro Gln Glu Tyr Cys Ile Phe Leu Tyr Asp Gly Ile Thr Lys Leu
                35                  40                  45
Thr Ser Ile Ser Glu Asn Gly Thr Ile Met Asn Leu Gln Tyr Tyr Lys
 50                  55                  60
Gly Ala Phe Val Ile Met Ser Gly Phe Ile Asp Thr Glu Thr Ser Val
 65                  70                  75                  80
Gly Tyr Tyr Asn Leu Glu Val Ile Ser Glu Gln Ala Thr Ala Tyr Val
                 85                  90                  95
Ile Lys Ile Asn Glu Leu Lys Glu Leu Leu Ser Lys Asn Leu Thr His
                100                 105                 110
Phe Phe Tyr Val Phe Gln Thr Leu Gln Lys Gln Val Ser Tyr Ser Leu
                115                 120                 125
Ala Lys Phe Asn Asp Phe Ser Ile Asn Gly Lys Leu Gly Ser Ile Cys
                130                 135                 140
Gly Gln Leu Leu Ile Leu Thr Tyr Val Tyr Gly Lys Glu Thr Pro Asp
145                 150                 155                 160
Gly Ile Lys Ile Thr Leu Asp Asn Leu Thr Met Gln Glu Leu Gly Tyr
                165                 170                 175
Ser Ser Gly Ile Ala His Ser Ser Ala Val Ser Arg Ile Ile Ser Lys
                180                 185                 190
Leu Lys Gln Glu Lys Val Ile Val Tyr Lys Asn Ser Cys Phe Tyr Val
                195                 200                 205
Gln Asn Leu Asp Tyr Leu Lys Arg Tyr Ala Pro Lys Leu Asp Glu Trp
                210                 215                 220
Phe Tyr Leu Ala Cys Pro Ala Thr Trp Gly Lys Leu Asn
225                 230                 235
```

-continued

```
<210> SEQ ID NO 17
<211> LENGTH: 237
<212> TYPE: PRT
<213> ORGANISM: Listeria monocytogenes

<400> SEQUENCE: 17

Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

Thr Ser Ile Ser Glu Asn Gly Thr Ile Met Asn Leu Gln Tyr Tyr Lys
    50                  55                  60

Gly Ala Phe Val Ile Met Ser Gly Phe Ile Asp Thr Glu Thr Ser Val
65                  70                  75                  80

Gly Tyr Tyr Asn Leu Glu Val Ile Ser Glu Gln Ala Thr Ala Tyr Val
                85                  90                  95

Ile Lys Ile Asn Glu Leu Lys Glu Leu Leu Ser Lys Asn Leu Thr His
            100                 105                 110

Phe Phe Tyr Val Phe Gln Thr Leu Gln Lys Gln Val Ser Tyr Ser Leu
        115                 120                 125

Ala Lys Phe Asn Asp Phe Ser Ile Asn Gly Lys Leu Gly Ser Ile Cys
    130                 135                 140

Gly Gln Leu Leu Ile Leu Thr Tyr Val Tyr Ser Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
            180                 185                 190

Leu Lys Gln Glu Lys Val Ile Val Tyr Lys Asn Ser Cys Phe Tyr Val
        195                 200                 205

Gln Asn Leu Asp Tyr Leu Lys Arg Tyr Ala Pro Lys Leu Asp Glu Trp
    210                 215                 220

Phe Tyr Leu Ala Cys Pro Ala Thr Trp Gly Lys Leu Asn
225                 230                 235

<210> SEQ ID NO 18
<211> LENGTH: 5
<212> TYPE: PRT
<213> ORGANISM: Listeria monocytogenes

<400> SEQUENCE: 18

Thr Glu Ala Lys Asp
1               5

<210> SEQ ID NO 19
<211> LENGTH: 5
<212> TYPE: PRT
<213> ORGANISM: Lactococcus lactis

<400> SEQUENCE: 19

Val Tyr Ala Asp Thr
1               5

<210> SEQ ID NO 20
<211> LENGTH: 5
<212> TYPE: PRT
<213> ORGANISM: Bacillus anthracis
```

```
<400> SEQUENCE: 20

Ile Gln Ala Glu Val
1               5

<210> SEQ ID NO 21
<211> LENGTH: 5
<212> TYPE: PRT
<213> ORGANISM: Listeria monocytogenes

<400> SEQUENCE: 21

Ala Ser Ala Ser Thr
1               5

<210> SEQ ID NO 22
<211> LENGTH: 5
<212> TYPE: PRT
<213> ORGANISM: Listeria monocytogenes

<400> SEQUENCE: 22

Val Gly Ala Phe Gly
1               5

<210> SEQ ID NO 23
<211> LENGTH: 5
<212> TYPE: PRT
<213> ORGANISM: Bacillus anthracis

<400> SEQUENCE: 23

Ala Phe Ala Glu Asp
1               5

<210> SEQ ID NO 24
<211> LENGTH: 5
<212> TYPE: PRT
<213> ORGANISM: Staphylococcus aureus

<400> SEQUENCE: 24

Val Gln Ala Ala Glu
1               5

<210> SEQ ID NO 25
<211> LENGTH: 5
<212> TYPE: PRT
<213> ORGANISM: Listeria monocytogenes

<400> SEQUENCE: 25

Asp Lys Ala Leu Thr
1               5

<210> SEQ ID NO 26
<211> LENGTH: 5
<212> TYPE: PRT
<213> ORGANISM: Bacillus subtillus

<400> SEQUENCE: 26

Val Gly Ala Phe Gly
1               5

<210> SEQ ID NO 27
<211> LENGTH: 29
<212> TYPE: PRT
<213> ORGANISM: Listeria monocytogenes

<400> SEQUENCE: 27
```

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala
            20                  25

<210> SEQ ID NO 28
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 29
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 30
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 30

```
Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100
```

<210> SEQ ID NO 31
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100
```

<210> SEQ ID NO 32
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60
```

```
Arg Glu Val Ser Ser Arg Asp Ile Glu Glu Leu Glu Lys Ser Asn Lys
 65                  70                  75                  80

Val Lys Asn Thr Asn Lys Ala Asp Leu Ile Ala Met Leu Lys Ala Lys
                 85                  90                  95

Ala Glu Lys Gly Gly Ser Ala Ser Lys Val Leu Pro Ala Ser Arg Ala
            100                 105                 110

Leu Glu Glu Lys Lys Gly Asn Tyr Val Val Thr Asp His Gly Ser Cys
        115                 120                 125

Ala Asp Gly Ser Val Lys Thr Ser Ala Ser Lys Val Ala Pro Ala Ser
    130                 135                 140

Arg Ala Leu Glu Glu Lys Lys Gly Asn Tyr Val Val Thr Asp His Gly
145                 150                 155                 160

Ser Cys Gly Asp Gly Ser Ile Lys Leu Ser Lys Val Leu Pro Ala Ser
                165                 170                 175

Arg Ala Leu Glu Glu Lys Lys Gly Asn Tyr Val Val Thr Asp His Gly
            180                 185                 190

Ser Cys Ala Asp Gly Ser Val Lys Ala Ser Lys Val Ala Pro Ala Ser
        195                 200                 205

Arg Ala Leu Glu Glu Lys Lys Gly Asn Tyr Val Val Thr Asp His Gly
    210                 215                 220

Ser Cys Gly Asp Gly Ser Ile Lys Leu Ser Lys Val Leu Pro Ala Ser
225                 230                 235                 240

Arg Ala Leu Glu Glu Lys Lys Gly Asn Tyr Val Val Thr Asp His Gly
                245                 250                 255

Ser Cys Ala Asp Gly Ser Val Lys Thr Ser
            260                 265

<210> SEQ ID NO 33
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gtgggattaa atagatttat gcgtgcgatg atggtagttt tcattactgc caactgcatt      60
acgattaacc ccgacataat atttgcagcg acagatagcg aagattccag tctaaacaca    120
gatgaatggg aagaagaaaa aacagaagag cagccaagcg aggtaaatac gggaccaaga    180
tacgaaactg cacgtgaagt aagttcacgt gatattgagg aactagaaaa atcgaataaa    240
gtgaaaaata cgaacaaagc agacctaata gcaatgttga agcaaaagc agagaaaggt     300 ggatccgcaa gcaaagtatt gccagctagt cgtgcattag aggagaaaaa ggggaattac    360
gtggtgacgg atcatggatc gtgtgccgat ggctcagtaa agactagtgc gagcaaagtg    420
gcccctgcat cacgagcact tgaagagaaa aaaggaaact atgttgtgac cgatcatggt    480
agctgcggag atggttcaat taaattatca aaagtcttac cagcatctag agctttagag    540
gaaaagaagg gtaactatgt cgtaacagat catggaagtt gtgctgacgg aagtgttaaa    600
gcgtcgaaag tagctccagc ttctcgcgca ttagaagaaa agaaaggcaa ttatgttgta    660
acagaccatg gtagttgtgg tgatggctcg atcaaattgt caaaagttct accggcttct    720
cgtgcgctag aagagaagaa aggaaattac gtagttacag accacggctc ttgcgcggat    780
ggttccgtta aaactagt                                                  798
```

<210> SEQ ID NO 34
<211> LENGTH: 221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
gggaagcagt tggggttaac tgattaacaa atgttagaga aaaattaatt ctccaagtga      60
tattcttaaa ataattcatg aatatttttt cttatattag ctaattaaga agataattaa     120
ctgctaatcc aattttttaac ggaataaatt agtgaaaatg aaggccgaat tttccttgtt    180
ctaaaaaggt tgtattagcg tatcacgagg agggagtata a                         221
```

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

```
Ala Thr Asp Ser Glu Asp Ser Ser Leu Asn Thr Asp Glu Trp Glu Glu
1               5                   10                  15
Glu Lys
```

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

```
Ser Ile Ile Asn Phe Glu Lys Leu
1               5
```

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Ala Arg Asn Asp Cys Gln Glu Gly His Ile
1               5                   10
```

<210> SEQ ID NO 38
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(30)

<400> SEQUENCE: 38

```
gca cgu aau gau ugu caa gaa ggu cau auu                               30
Ala Arg Asn Asp Cys Gln Glu Gly His Ile
1               5                   10
```

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Lys Met Phe Pro Ser Thr Trp Tyr Val
1               5                   10

<210> SEQ ID NO 40
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)

<400> SEQUENCE: 40 uua aaa aug uuu cca agu aca ugg uau guu                             30
Leu Lys Met Phe Pro Ser Thr Trp Tyr Val
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Ala Ser Arg Ala Leu Glu Glu Lys Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Tyr Val Val Thr Asp His Gly Ser Cys
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Ala Ser Arg Ala Leu Glu Glu Lys Lys Gly Asn Tyr Val Val
1               5                   10                  15

<210> SEQ ID NO 44
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 44

Ala Ser Arg Ala Leu Glu Glu Lys Lys Gly Asn Tyr Val Val Thr
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Arg Ala Leu Glu Glu Lys Lys Gly Asn Tyr Val Val Thr Asp
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Leu Glu Glu Lys Lys Gly Asn Tyr Val Val Thr Asp His
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Leu Glu Glu Lys Lys Gly Asn Tyr Val Val Thr Asp His Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu Glu Lys Lys Gly Asn Tyr Val Val Thr Asp His Gly Ser
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Glu Lys Lys Gly Asn Tyr Val Val Thr Asp His Gly Ser Cys
1               5                   10                  15
```

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Lys Lys Gly Asn Tyr Val Val Thr Asp His Gly Ser Cys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Lys Gly Asn Tyr Val Val Thr Asp His Gly Ser Cys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Gly Asn Tyr Val Val Thr Asp His Gly Ser Cys
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Asn Tyr Val Val Thr Asp His Gly Ser Cys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Tyr Val Val Thr Asp His Gly Ser Cys
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 55

Tyr Val Val Thr Asp His Gly Ser Cys
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Val Thr Asp His Gly Ser Cys
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Glu Lys Lys Gly Asn Tyr
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Glu Lys Lys Gly Asn Tyr Val Val
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Glu Lys Lys Gly Asn Tyr Val Val Thr
1               5                   10
```